(12) United States Patent
Lee et al.

(10) Patent No.: US 7,297,538 B2
(45) Date of Patent: Nov. 20, 2007

(54) ENCAPSULATED CELL INDICATOR SYSTEM

(75) Inventors: Ike W. Lee, Norwood, MA (US); Jeffrey D. Croissant, Eugene, OR (US); Rabia Ballica, Gaithersburg, MD (US)

(73) Assignee: Cardio3 S.A., Braine-l'Alleud (BE)

( * ) Notice: Subject to any disclaimer, the term of this patent is extended or adjusted under 35 U.S.C. 154(b) by 578 days.

(21) Appl. No.: 10/121,295

(22) Filed: Apr. 12, 2002

(65) Prior Publication Data

US 2003/0017510 A1    Jan. 23, 2003

Related U.S. Application Data

(60) Provisional application No. 60/283,838, filed on Apr. 13, 2001.

(51) Int. Cl.
C12N 5/00 (2006.01)
C12N 5/02 (2006.01)
C12N 5/08 (2006.01)

(52) U.S. Cl. ............... 435/325; 435/382; 435/366

(58) Field of Classification Search ........... 435/325; 424/93.1
See application file for complete search history.

(56) References Cited

U.S. PATENT DOCUMENTS

| | | | |
|---|---|---|---|
| 5,197,985 | A | 3/1993 | Caplan et al. |
| 5,199,942 | A | 4/1993 | Gillis |
| 5,202,120 | A | 4/1993 | Silver et al. |
| 5,226,914 | A | 7/1993 | Caplan et al. |
| 5,294,446 | A | 3/1994 | Schlameus et al. |
| 5,486,359 | A | 1/1996 | Caplan et al. |
| 5,543,318 | A | 8/1996 | Smith et al. |
| 5,580,779 | A | 12/1996 | Smith et al. |
| 5,591,625 | A | 1/1997 | Gerson et al. |
| 5,602,301 | A | 2/1997 | Field |
| 5,733,727 | A | 3/1998 | Field |
| 5,736,396 | A | 4/1998 | Bruder et al. |
| 5,908,623 | A | 6/1999 | Baetge et al. |
| 5,935,849 | A | 8/1999 | Schinstine et al. |
| 5,942,225 | A | 8/1999 | Bruder et al. |
| 6,099,832 | A | 8/2000 | Mickle et al. |
| 6,110,459 | A | 8/2000 | Mickle et al. |
| 6,818,757 | B2 | 11/2004 | Lee et al. |
| 2003/0031651 | A1 | 2/2003 | Lee et al. |

FOREIGN PATENT DOCUMENTS

| | | |
|---|---|---|
| EP | 1 254 952 A1 | 11/2002 |
| WO | WO 95/12979 A1 | 5/1995 |
| WO | WO 95/14079 A1 | 5/1995 |
| WO | WO 95/34581 A1 | 12/1995 |
| WO | WO 99/03973 A1 | 1/1999 |
| WO | WO 00/17326 A1 | 3/2000 |
| WO | WO 02/083864 A2 | 10/2002 |
| WO | WO 02/083864 A3 | 10/2002 |
| WO | WO 02/084281 A1 | 10/2002 |
| WO | WO 2004/065589 A1 | 8/2004 |
| WO | WO 2005/056779 A1 | 6/2005 |

OTHER PUBLICATIONS

Ducret et al. (1999) The Net Repressor is regulated by nuclear export in response to Anisomycin, UV, and Heat Shock. Molecular and Cellular Biology. 19:7076-7087.*

Heinrichs et al. (1993) Identification and Characterization of Two Proximal Elements in the Rat Osteocalcin Gene Promoter That May Confer Species-Specific Regulation. J. Cell. Biochem53:240-250.*

Shi et al. (1999) Species-Specific differences in postive and negative regulatory elements in the reniin gene enhancer. Circ. Res. 85:479-488.*

Levee et al., "Microencapsulated human bone marrow cultures: a potential culture system for the clonal outgrowth of hematopoietic progenitor cells," *Biotechnology and Bioengineering* 43:734-739 (1994).

Ross et al., "Somatic gene therapy for a neurodegenerative disease using microencapsulated recombinant cells," *Experimental Neurology* 166:276-286 (2000).

U.S. Appl. No. 10/542,757, filed Dec. 30, 2003, Croissant et al.

Asahara et al., "Isolation of Putative Progenitor Endothelial Cells for Angiogenesis," *Science* 275:964-967 (1997).

Baksh et al., "Soluble Factor Cross-Talk between Human Bone Marrow-Derived Hematopoietic and Mesenchymal Cells Enhances In Vitro CFU-F and CFU-O Growth and Reveals Heterogeneity in the Mesenchymal Progenitor Cell Compartment," *Blood* 106:3012-3019 (2005).

Balsam et al., "Haematopoietic Stem Cells Adopt Mature Haematopoietic Fates in Ischaemic Myocardium," *Nature* 428:668-673 (2004).

Caplan, "Mesenchymal Stem Cells," *J. Orthop. Res.* 9:641-650 (1991).

Chiu et al., "Cellular Cardiomyoplasty: Myocardial Regeneration with Satellite Cell Implantation," *Ann. Thorac. Surg.* 60:12-18 (1995).

Christlieb, "Cellular Cardiomyoplasty," *Ann. Thorac. Surg.* 61:772-773 (1996).

(Continued)

*Primary Examiner*—Valarie Bertoglio
(74) *Attorney, Agent, or Firm*—Clark & Elbing, LLP

(57) ABSTRACT

The invention features an encapsulated cell indicator system that includes (a) indicator cells having a signal-responsive element operably linked to a reporter gene; (b) encapsulating material; and (c) a permeable membrane. In this encapsulated cell indicator system, the indicator cells are encapsulated in the encapsulated material and the encapsulated material and the indicator cells are surrounded by the permeable membrane.

19 Claims, 23 Drawing Sheets
(13 of 23 Drawing Sheet(s) Filed in Color)

OTHER PUBLICATIONS

Clark et al., "Biology of Bone Marrow Stroma," *Ann. NY Acad. Sci.* 770:70-78 (1995).
Florini et al., "Effects of Growth Factors on Myogenic Differentiation," *Am. J. Physiol.* 256:C701-C711 (1989).
Goguen and Kedersha, "Clonogenic Cytotoxicity Testing by Microdrop Encapsulation," *Nature* 363:189-190 (1993).
Grigoriadis et al., "Differentiation of Muscle, Fat, Cartilage, and Bone from Progenitor Cells Present in a Bone-Derived Clonal Cell Population: Effect of Dexamethasone," *J. Cell Biol.* 106:2139-2151 (1988).
Gussoni et al., "Normal Dystrophin Transcripts Detected in Duchenne Muscular Dystrophy Patients after Myoblast Transplantation," *Nature* 356:435-438 (1992).
Haynesworth et al., "Characterization of Cells with Osteogenic Potential from Human Marrow," *Bone* 13:81-88 (1992).
Jacobson and Piper, "Cell Cultures of Adult Cardiomyocytes as Models of the Myocardium," *J. Mol. Cell. Cardiol.* 18:661-678 (1986).
Kao et al., "Satellite Cells for Myocardial Regeneration," *Physiologist* 32:220 (1989).
Kao et al., "Muscle Regeneration of Injured Myocardium," *J. Cell. Biochem.* 15C(Supp):73(F420) (1991).
Kao, "Regeneration of Injured Myocardium from Implanted Satellite Cells," *Circulation* 84(Supp II):II386(1539) (1991).
Keating et al., "Effect of Different Promoters on Expression of Genes Introduced into Hematopoietic and Marrow Stromal Cells by Electroporation," *Exp. Hematol.* 18:99-102 (1990).
Kim et al., "Surgical Angiogenesis Induced by Autologous Cell Transplantation," *Soc. Thorac. Surg. 35th Ann. Mtg.*, San Antonio, TX : 248(C6) (1999).
Koh et al., "Differentiation and Long-Term Survival of C2C12 Myoblast Grafts in Heart," *J. Clin. Invest.* 92:1548-1554 (1993).
Krance et al., "Hematopoietic and Immunomodulatory Effects of Lytic CD45 Monoclonal Antibodies in Patients with Hematologic Malignancy," *Biol. Blood Marrow Transplant.* 9:273-281 (2003).
Kruppenbacher et al., "Cardiomyocytes of Adult Mice in Long-Term Culture," *Naturwissenschaften* 80:132-134 (1993).
Laflamme and Murry, "Regenerating the Heart," *Nat. Biotechnol.* 23:845-856 (2005).
Leiden, "Beating the Odds: A Cardiomyocyte Cell Line at Last," *J. Clin. Invest.* 103:591-592 (1999).
Leor et al., "Transplantation of Fetal Myocardial Tissue into the Infarcted Myocardium of Rat: A Potential Method for Repair of Infarcted Myocardium?" *Circulation* 94(Supp II):II332-II336 (1996).
Li et al., "Method of Culturing Cardiomyocytes from Human Pediatric Ventricular Myocardium," *J. Tiss. Cult. Mech.* 14:93-100 (1992).
Li et al., "Effect of Donor Age on Contractility of Transplanted Rat Cardiomyocytes," *J. Mol. Cell. Cardiol.* 26:XCCI(162) (1994).
Li et al., "Cardiomyocyte Transplantation Improves Heart Function," *Ann. Thorac. Surp.* 62:654-661 (1996).
Li et al., "Human Pediatric and Adult Ventribular Cardiomyocytes in Culture: Assessment of Phenotypic Changes with Passaging," *Cardiovasc. Res.* 32:362-373 (1996).
Li et al., "In Vivo Survival and Function of Transplanted Rat Cardiomyocytes," *Circ. Res.* 78:283-288 (1996).
Li et al., "Natural History of Fetal Rat Cardiomyocytes Transplanted into Adult Rat Myocardial Scar Tissue," *Circulation* 96(Supp II):II179-II187 (1997).
Li et al., "Autologous Cardiomyocyte Transplantation Improved Porcine Heart Function after a Myocardial Infarction," *Am. Assoc. Thorac. Surg. 79th Ann. Mtg.*, New Orleans, LA : 120(34) (1999).
Li et al., "Development of an Autologous Bioengineered Cardiac Graft," *Am. Assoc. Thorac. Surg. 79th Ann. Mtg.*, New Orleans, LA : 190(F12) (1999).
Li et al., "Smooth Muscle Cell Transplantation into Myocardial Scar Tissue Improves Heart Function," *J. Mol. Cell. Cardiol.* 31:513-522 (1999).
Li et al., "Survival and Function of Bioengineered Cardiac Grafts," *Circulation* 100(Supp II):II63-II69 (1999).

Lough et al., "Combined BMP-2 and FGF-4, but Neither Factor Alone, Induces Cardiogenesis in Non-Precardiac Embryonic Mesoderm," *Dev. Biol.* 178:198-202 (1996).
Lu et al., "Regulation of Skeletal Myogenesis by Association of the MEF2 Transcription Factor with Class II Histone Deacetylases," *Mol. Cell* 6:233-244 (2000).
Makino et al., "Cardiomyocytes Can Be Generated from Marrow Stromal Cells In Vitro," *J. Clin. Invest.* 103:697-705 (1999).
Marelli et al., "Cell Transplantation for Myocardial Repair: An Experimental Approach," *Cell Transplant.* 1:383-390 (1992).
Marelli et al., "Satellite Cell Implantation for Neo-Myocardial Regeneration," *Cell Transplant.* 1:Abstract No. 197 (1992).
Metzger et al., "Regenerative Capacity of Transplanted Cardiac Muscle in the Rat," *Acta Anat.* 125:180-182 (1986).
Monzen et al., "Bone Morphogenetic Proteins Induce Cardiomyocyte Differentiation through the Mitogen-Activated Protein Kinase Kinase Kinase TAK1 and Cardiac Transcription Factors Csx/Nkx-2.5 and GATA-4," *Mol. Cell. Biol.* 19:7096-7105 (1999).
Muguruma et al., "In Vivo and In Vitro Differentiation of Myocytes from Human Bone Marrow-Derived Multipotent Progenitor Cells," *Exp. Hematol.* 31:1323-1330 (2003).
Murry et al., "Haematopoietic Stem Cells Do Not Transdifferentiate into Cardiac Myocytes in Myocardial Infarcts," *Nature* 428:664-668 (2004).
Murry et al., "Skeletal and Cardiac Myoblast Transplantation after Myocardial Necrosis: Possible Routes to Muscle Regeneration," *Circulation* 92(Supp I):I12(0056) (1995).
Murry et al., "Skeletal Myoblast Transplantation for Repair of Myocardial Necrosis," *J. Clin. Invest.* 98:2512-2523 (1996).
Orlic et al., "Bone Marrow Cells Regenerate Infarcted Myocardium," *Nature* 410:701-705 (2001).
Pittenger et al., "Multilineage Potential of Adult Human Mesenchymal Stem Cells," *Science* 284:143-146 (1999).
Prockop, "Marrow Stromal Cells as Stem Cells for Nonhematopoietic Tissues," *Science* 276:71-74 (1997).
Reinecke et al., "Integration and Differentiation of Cardiocytes after Grafting Into Normal and Injured Myocardium," *Circulation* 96(Supp):I19(100) (1997).
Reyes et al., "Purification and Ex Vivo Expansion of Postnatal Human Marrow Mesodermal Progenitor Cells," *Blood* 98:2615-2625 (2001).
Sachinidis et al., "Generation of Cardiomyocytes from Embryonic Stem Cells," *Herz* 27:589-597 (2002).
Saito et al., "Myogenic Expression of Mesenchymal Stem Cells within Myotubes of *mdx* Mice In Vitro and In Vivo," *Tissue Eng.* 1:327-343 (1995).
Sakai et al., "A Comparison of Three Fetal Cell Types for Transplantation into a Myocardial Scar to Improve Heart Function," *Am. Assoc. Thorac. Surg. 79th Ann. Mtg.*, New Orleans, LA : 110(L5) (1999).
Sakai et al., "Autologous Cardiomyocyte Transplantation Improves Cardiac Function after Myocardial Injury," *Soc. Thorac. Surg. 35th Ann. Mtg.*, San Antonio, TX : 76(12) (1999).
Sakai et al., "Autologous Heart Cell Transplantation Improves Cardiac Function after Myocardial Injury," *Ann. Thorac. Surg.* 68:2074-2081 (1999).
Sakai et al., "Fetal Cell Transplantation: A Comparison of Three Cell Types," *J. Thorac. Cardiovasc. Surg.* 1.18:715-725 (1999).
Scorsin et al., "Can Grafted Cardiomyocytes Colonize Peri-Infarct Myocardial Areas?" *Circulation* 94(Supp II):II337-II340 (1996).
Soonpaa et al., "Formation of Nascent Intercalated Disks between Grafted Fetal Cardiomyocytes and Host Myocardium," *Science* 264:98-101 (1994).
Thompson, "Fetal Transplants Show Promise," *Science* 257:868-870 (1992).
Tomita et al., "Autologous Transplantation of Bone Marrow Cells Improves Damaged Heart Function," *Circulation* 100(Supp II):II247-II256 (1999).
Uludag et al., "Technology of Mammalian Cell Encapsulation," *Adv. Drug Deliv. Rev.* 42:29-64 (2000).
Wakitani et al., "Myogenic Cells Derived from Rat Bone Marrow Mesenchymal Stem Cells Exposed to 5-Azacytidine," *Muscle Nerve* 18:1417-1426 (1995).

Yau et al., "Heart Cell Transplantation for the Failing Heart," in *State of the Heart: The Practical Guide to Your Heart and Heart Surgery*. Stephenson and Rodengen (eds.), Write Stuff Enterprises: Fort Lauderdale, pp. 202-208 (1999).

Yoon et al., "Myocardial Regeneration: Transplanting Satellite Cells into Damaged Myocardium," *Tex. Heart Inst. J.* 22:119-125 (1995).

Young et al., "Pluripotent Mesenchymal Stem Cells Reside within Avian Connective Tissue Matrices," *In Vitro Cell. Dev. Biol.* 29A:723-736 (1993).

* cited by examiner

Figure 4
In vitro Dog BMSCs Differentiation
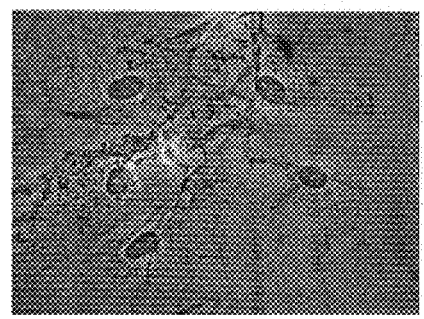 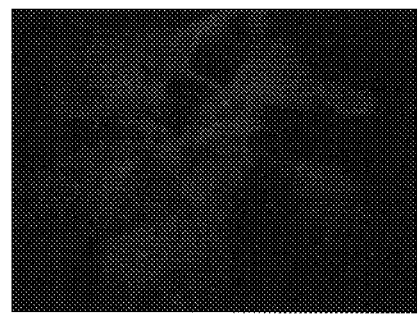
Phase　　　　　　　　Csx Immunostaining Expression of an Endothelial Cell Marker in In Vitro Differentiated Mouse BMSCs Detection of the Implanted BMSCs in the Infarct Area
of a Dog Heart (15 Days Post-implantation)

Detection of the Implanted BMSCs in the Infarct Area
of a Dog Heart (15 Days Post-implantation)

Detection of the Implanted BMSCs in the Infarct Area
of a Dog Heart (15 Days Post-implantation)

Detection of the Implanted BMSCs in the Infarct Area
of a Dog Heart (15 Days Post-implantation)

Incorporation of injected cells into myocardium of infarcted mouse heart (36 days after injection with treatments)

Incorporation of injected cells into myocardium of infarcted mouse heart (36 days after injection with treatments)

Incorporation of injected cells into myocardium of infarcted mouse heart (36 days after injection with treatments)

Incorporation of injected cells into myocardium of infarcted mouse heart (36 days after injection with treatments)

Incorporation of injected cells into myocardium of infarcted mouse heart (36 days after injection with treatments)

Figure 15
Differentiation of the BMSCs from hCsx-lacZ Mouse
(to be used in the Cell Differentiation Indicator System)
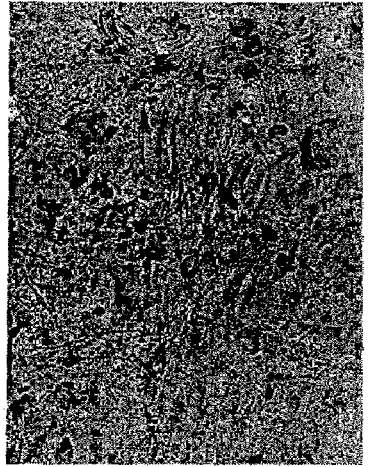
Induced Differentition
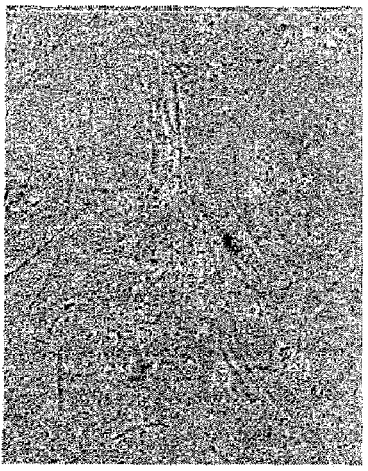
Autodifferentiation Figure 17
Echocardiogram of an Infarcted Dog Heart
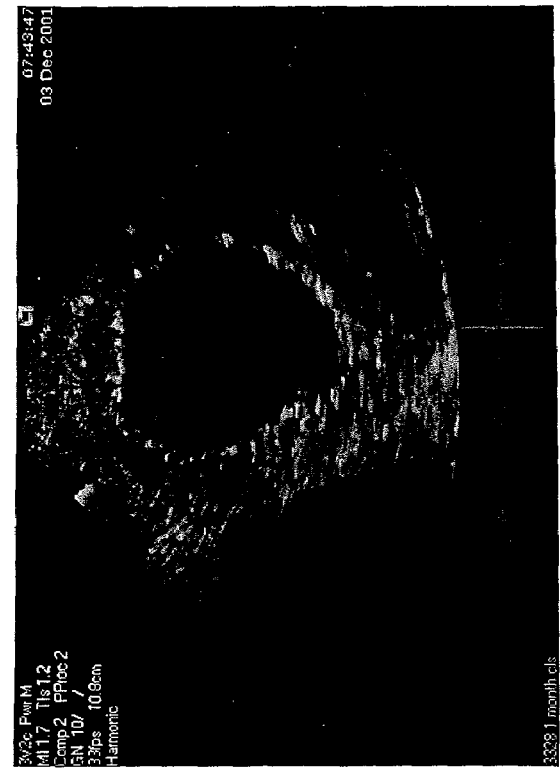
Baseline (#3328)
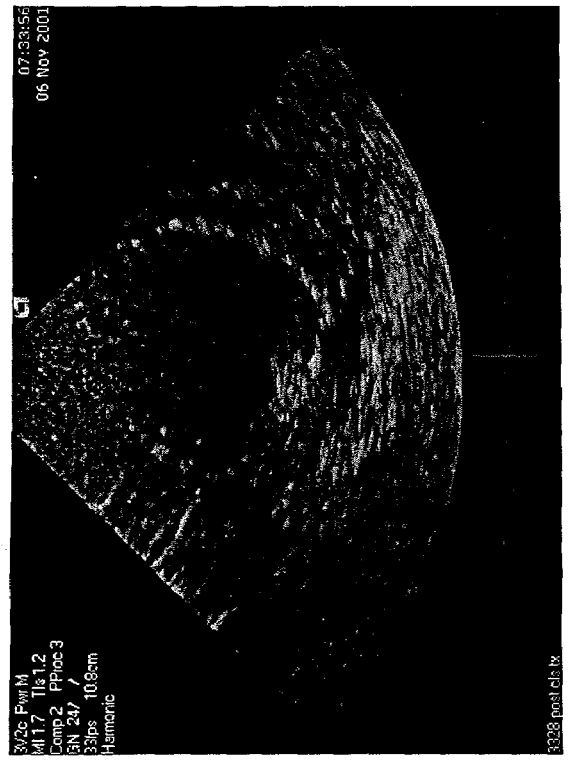
4.5 Weeks after Cell Injection Figure 18  Echocardiogram of an Infarcted Dog Heart
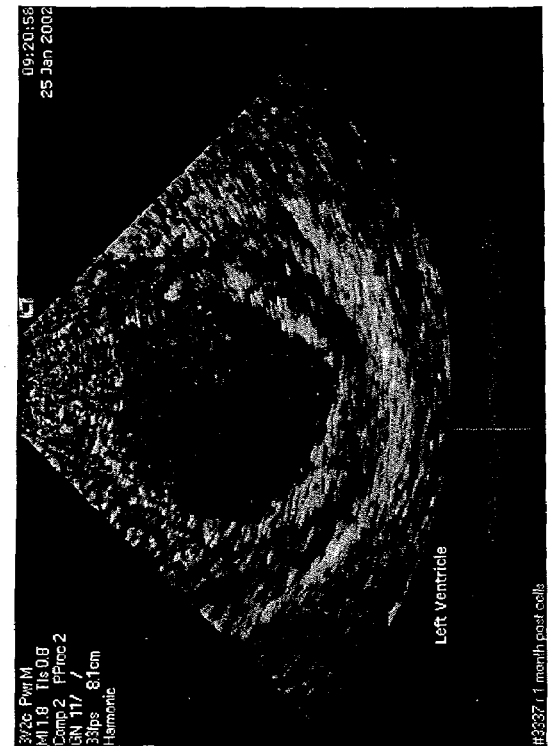
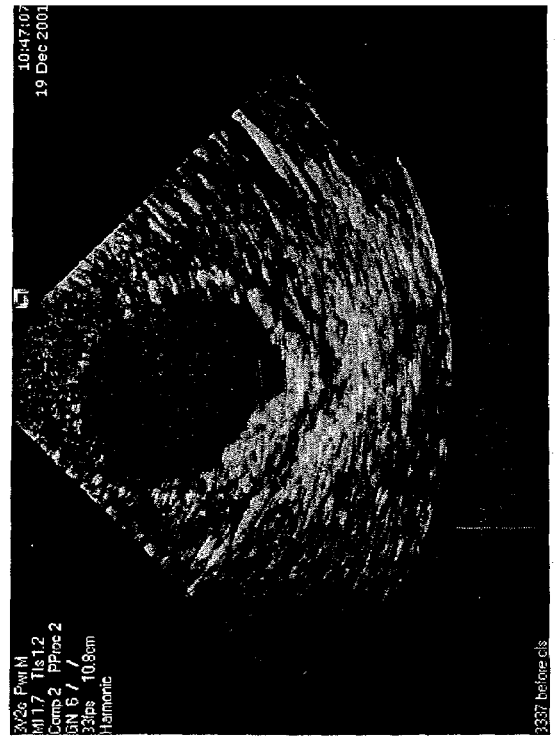
Baseline (#3337)   5 Weeks after Cell Injection Figure 19    Echocardiogram of an Infarcted Dog Heart
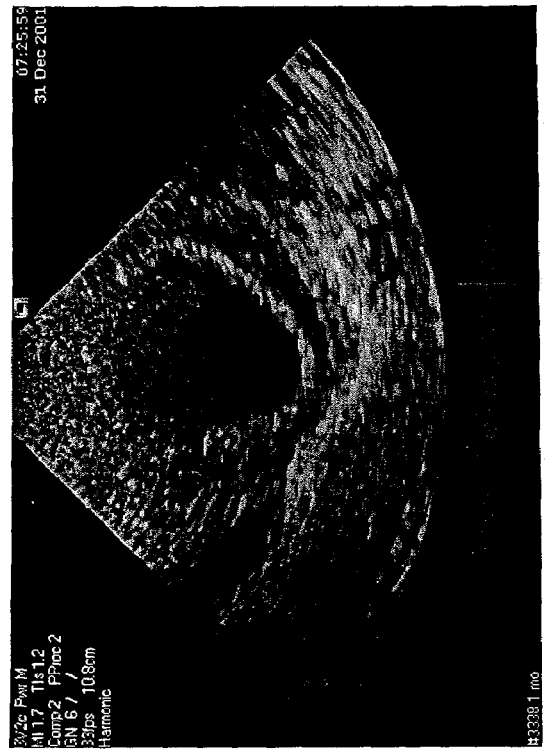
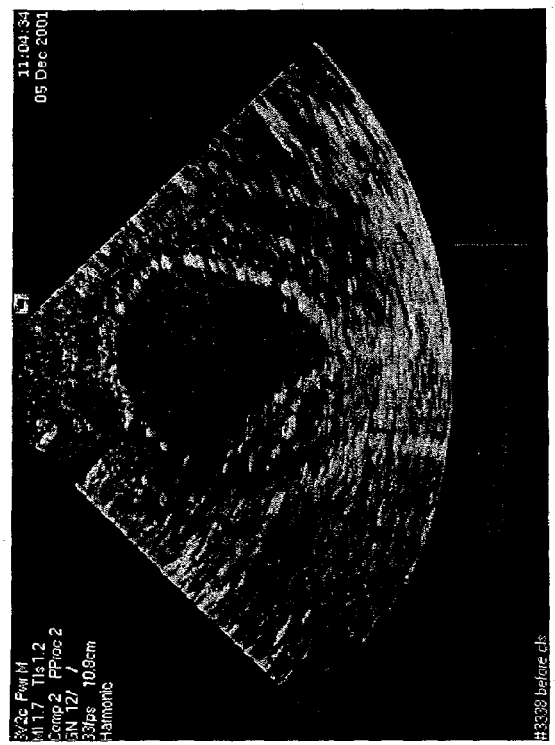
Baseline (#3338)    3.5 Weeks after Cell Injection

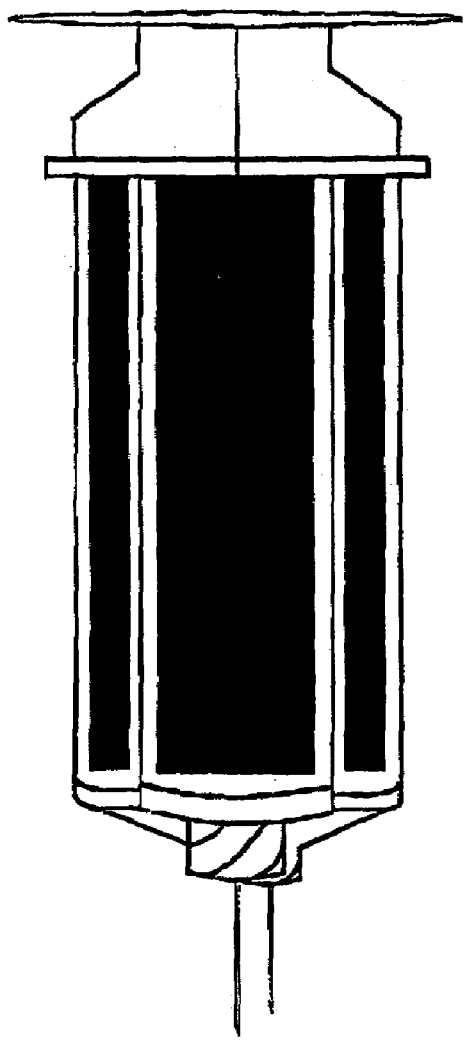
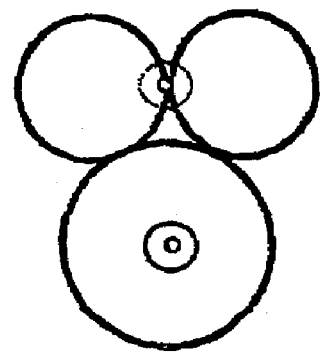
Fig. 21B
Fig. 21A

ENCAPSULATED CELL INDICATOR SYSTEM

CROSS REFERENCE TO RELATED APPLICATIONS

This application claims benefit of the filing date of copending application U.S. Provisional Patent Application No. 60/283,838 (filed Apr. 13, 2001), hereby incorporated by reference.

BACKGROUND OF THE INVENTION

The invention relates to the field of cell transplantation.

The possibility of bone marrow being an in vivo source of circulating cardiomyocyte progenitors has been suggested. In one experiment, transplanted bone marrow-derived cells were observed to be distributed in a dystrophic mouse heart. Although the molecular characteristics of these cells were not identified, their location in the heart tissue indicated these cells were cardiomyocytes. The ability of bone marrow mesenchymal stem cells (BMSCs) to differentiate as beating cardiomyocytes following introduction of inductive agents such as 5-azacytidine has also been shown. Based on these findings, BMSCs have been proposed to be a source of cells for treatment of cardiac disease and cardiac abnormalities.

Despite the potential therapeutic value of BMSCs, current cell transplantation methods for cardiac tissue are clinically inadequate because rate of implant incorporation into the host tissue is poor. For example, Orlic et al. (Nature 410: 701-705, 2001) reported that only 40% of mice receiving BMSC transplants showed some myocardial repair.

Thus, there is a need for preparing cells for cell transplantation such that there are high rates of cell incorporation and cell survival.

SUMMARY OF THE INVENTION

We have discovered a biologically active indicator system with which to determine, in real time and in a non-destructive manner, the differentiation state of cells in culture. This indicator cell system allows determination of the differentiation of a first population of cells being cultured, for example, for transplantation without genetically or otherwise modifying this population to be transplanted. The cell indicator system includes (a) indicator cells having a signal-responsive element operably linked to a reporter gene; (b) encapsulating material; and (c) a permeable membrane. The cell indicator system is co-cultured with the first population of cells. The extent of reporter gene expression in the indicator system correlates with the differentiation state of the second population of cells. Once the reporter gene expression reaches a desired level or the reporter gene is expressed in a certain percentage of indicator cells, the second population is collected for use, for example, in cell transplantation.

Accordingly, in a first aspect, the invention features an encapsulated cell indicator system that includes (a) indicator cells having a signal-responsive element operably linked to a reporter gene; (b) encapsulating material; and (c) a permeable membrane. In this encapsulated cell indicator system, the indicator cells are encapsulated in the encapsulating material and the encapsulating material and the indicator cells are surrounded by the permeable membrane.

The indicator cells can include, for example, embryonic stem cells or bone marrow stem cells. While it is desirable that the indicator cells be human cells, they can be from any mammal (e.g., a mouse or a pig). In one embodiment, the cells are the same as the first population of cells, differing in that they include the signal-responsive element and the reporter gene. Any reporter gene can be used in the indicator system, so long as the reporter gene is present in a construct which allows for the reporter gene to be differentially expressed at the stage at which it is desirable to collect the first population. It is preferable that the detection of the reporter gene expression can be accomplished by a method having no substantial toxicity to the cells (e.g., enzymatic and fluorogenic detection methods). Exemplary reporter genes include those encoding β-galactosidase, green fluorescent protein, and luciferase. Suitable encapsulating materials include, without limitation, alginate, collagen, gelatin, and chitosan. The encapsulating material can also be, for example, a biodegradable polymer such as polylactic acid (PLA), polyglycolic acid (PGA), or polylactide/glycolide copolymer (PLGA). Exemplary permeable membranes include porous transparent polyethylene terephthalate (PET) membrane, transparent nylon mesh, transparent porous nylon membrane, and porous transparent polytetrafluoroethylene (PTFE/Teflon).

In a second aspect, the invention features a method of determining the state of cells in culture without a substantial loss in viability. This method includes (a) providing a culture that includes a population of cells and the encapsulated cell indicator system of the first aspect, wherein the expression of the reporter gene correlates with the state of differentiation of the population of cells; and (b) measuring the expression of the reporter gene using a method that does not result in substantial loss of viability of the population of cells, wherein the expression level of the reporter gene is indicative of the state of differentiation of the population of cells.

Cells in a particular state of the state of differentiation and suitable genes from which a signal-responsive element can be derived are listed below. Vascular smooth muscle cell: Bves; Endothelial cell: Tie-2, von Willebrand factor; epicardial cell: Flk-1, ICAM-2; adipocyte: PPAR-γ2; osteoclast: TRAP' osteoblast: osteocalcin; macrophage: CD11b; neuronal progenitor: nestin; neuron: neurofilament; astrocyte: GFAP; skeletal muscle cell: MyoD; smooth muscle cell: SMHC; pancreatic precursor cell: Pdx-1; pancreatic β-cell: hepatocyte: α-fetoprotein.

By "non-destructive," when referring to an indicator system, is meant a method that results in less than a 10% loss of cultured cells. Specifically, non-destructive indicators do not require killing the cells of an entire culture vessel in order to determine their state of differentiation.

By "stem cell" is meant a cell capable of (i) self renewing, and (ii) producing multiple differentiated cell types, including one of the group selected from cardiomyocyte, endothelial cell, and vascular smooth muscle cell.

By "BMSC" is meant a bone marrow mesenchyme-derived stem cell that is CD45$^-$. BMSCs are also referred to as "bone marrow stem cells" and "bone marrow multipotent progenitor cells."

As used herein, by "nucleic acid" is meant either DNA or RNA. A "nucleic acid molecule" may be a single-stranded or double-stranded polymer of deoxyribonucleotide or ribonucleotide bases. Unless otherwise specified, the left hand direction of the sequence of a single-stranded nucleic acid molecule is the 5' end, and the left hand direction of double-stranded nucleic molecule is referred to as the 5' direction.

By "Csx/Nkx2.5" is meant a nucleic acid or polypeptide that is substantially identical to the mouse or human Csx/

Nkx2.5 cDNA or Csx/Nkx2.5 polypeptide and, when expressed in BMSCs, induces the cells to become cardiomyogenic. Desirably, the nucleic acid shares at least 80% identity with mouse or human Csx/Nkx2.5 over a stretch of 50 consecutive nucleotides, more desirably at least 85%, and more desirably at least 90% or even 95% identity. Gaps of up to 10% may be included in one or both of the sequences. Desirably, the polypeptide shares at least 80% identity with mouse or human Csx/Nkx2.5 over a stretch of 25 consecutive amino acids, more desirably at least 85%, and more desirably at least 90% or even 95% identity. Again, gaps of up to 10% may be included in one or both of the sequences.

By "treating" is meant reducing or alleviating at least one adverse effect or symptom of a disorder characterized by insufficient cardiac function. Adverse effects or symptoms of cardiac disorders are numerous and well-characterized. Non-limiting examples of adverse effects or symptoms of cardiac disorders include: dyspnea, chest pain, palpitations, dizziness, syncope, edema, cyanosis, pallor, fatigue, and death. For additional examples of adverse effects or symptoms of a wide variety of cardiac disorders, see Robbins, S. L. et al. (1984) Pathological Basis of Disease (W. B. Saunders Company, Philadelphia) 547-609; and Schroeder, S. A. et al. eds. (1992) Current Medical Diagnosis & Treatment (Appleton & Lange, Connecticut) 257-356.

By "disorder characterized by insufficient cardiac function" includes an impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte or a population of cardiomyocytes. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, transmission of electrical impulses in abnormal patterns or at abnormal times, and an altered chamber pressure resulting from one of the aforementioned abnormalities. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, cardiomyopathy, cardiac disorders which result in congestive heart failure, and tumors of the heart, e.g., primary sarcomas and secondary tumors.

"Administering," "introducing," and "transplanting" are used interchangeably and refer to the placement of the cardiomyogenic cells of the invention into a subject, e.g., a human subject, by a method or route which results in localization of the cells at a desired site.

By "promoter" is meant a region of nucleic acid, upstream from a translational start codon, which is involved in recognition and binding of RNA polymerase and other proteins to initiate transcription. A "human promoter" is a promoter capable of initiating transcription in a human cell, and may or may not be derived from a human cell. A "Csx/Nkx2.5 promoter" is one derived from the promoter region of a Csx/Nkx2.5 gene and that, when operably linked to a heterologous nucleic acid molecule, is capable of initiating transcription of that molecule (when present in a transcription medium capable of supporting transcription) in a cardiac cell.

By "enhancer element" or "enhancer" is meant a nucleic acid sequence that, when positioned proximate to a promoter and present in a transcription medium capable of supporting transcription, confers increased transcription activity relative to the transcription activity resulting from the promoter in the absence of the enhancer domain. A "Csx/Nkx2.5 enhancer" is one derived from the promoter region of a Csx/Nkx2.5 gene and that, when operably linked to a heterologous nucleic acid molecule, is capable of initiating transcription of that molecule (when present in a transcription medium capable of supporting transcription) in a cardiac cell. A "Tie-2 enhancer" is one derived from the promoter region of a Tie-2 gene and that, when operably linked to a heterologous nucleic acid molecule, is capable of initiating transcription of that molecule (when present in a transcription medium capable of supporting transcription) in an endothelial cell. A "Bves enhancer" is one derived from the promoter region of a Bves gene and that, when operably linked to a heterologous nucleic acid molecule, is capable of initiating transcription of that molecule (when present in a transcription medium capable of supporting transcription) in a vascular smooth muscle cell.

By "operably linked" is meant that two or more nucleic acid molecules (e.g., a nucleic acid molecule to be transcribed, a promoter, and an enhancer element) are connected in such a way as to permit transcription of the nucleic acid molecule in a suitable transcription medium.

By "derived from" is meant that a the nucleic acid molecule was either made or designed from a second nucleic acid molecule, the derivative retaining at least one important function of the nucleic acid molecule from which it was made or designed.

By "expression construct" is meant a nucleic acid molecule that supports transcription. An expression construct of the present invention includes, at the least, a cardiac-specific enhancer element and a promoter. Additional elements, such as a transcription termination signal, may also be included, as described herein.

By "vector" or "expression vector" is meant an expression system, a nucleic acid-based vehicle, a nucleic acid molecule adapted for nucleic acid delivery, or an autonomous self-replicating circular DNA (e.g., a plasmid). When a vector is maintained in a host cell, the vector can either be stably replicated by the cells during mitosis as an autonomous structure, incorporated within the genome of the host cell, or maintained in the host cell's nucleus or cytoplasm.

By "cardiac cell" is meant a differentiated cardiac cell (e.g., a cardiomyocyte) or a cell committed to producing or differentiating as a cardiac cell (e.g., a cardiomyoblast or a cardiomyogenic cell).

By "cardiomyocyte" is meant a muscle cell in heart that expresses detectable amounts of cardiac markers (e.g., alpha-myosin heavy chain, cTnI, MLC2v, alpha-cardiac actin, and, in vivo, Cx43), contracts, and does not proliferate.

By "cardiomyoblast" is meant a cell that expresses detectable amounts cardiac markers, contracts, and proliferates.

By "cardiomyogenic cell" is meant a cell expressing detectable amounts of Csx/Nkx2.5 RNA or protein, and does not show organized sarcomeric structures or contractions, and preferably does not express detectable amounts of myosin heavy chain protein.

By "epicardial cell" is meant a cell that expresses detectable amounts of Flk-1 and/or ICAM-2, and can become an endothelial cell.

By "endocardial cell" is meant a cardiac cell that expresses detectable amounts of Tie-2 and/or von Willebrand Factor.

By "endothelial cell" is meant a cell that expresses detectable amounts of at least one of the following RNAs or proteins: MUC18, VE-cadherin, N-cadherin, alpha- and beta-catenins, Flk-1, Tie-2, and CD34.

By "cells primed to differentiate as endothelial cells" is meant stem cells that have not been immortalized that were cultured under conditions that induce the cells to become endothelial cells, wherein at least about 10%, 25%, 50%, 75%, 90%, 95%, 99%, or even 100% of the cells are endothelial cells.

By "cells primed to differentiate as vascular smooth muscle cells" is meant stem cells that have not been immortalized that were cultured under conditions that induce the cells to become vascular smooth muscle cells, wherein at least about 10%, 25%, 50%, 75%, 90%, 95%, 99%, or even 100% of the cells are vascular smooth muscle cells.

By "specifically induce one cell type" when referring to differentiation of cultured BMSCs is meant a culture wherein at least 50% of BMSCs differentiate into the desired cell type (i.e., cardiomyocytes).

By "detectable amounts" of a protein is meant an amount of a protein that is detectable by immunocytochemistry using, for example, the methods provided herein. One method for determining whether a cell is detectably labeled with either CsX/Nkx2.5 or myosin heavy chain is provided below. Cultured cells are fixed with 4% formaldehyde for 20 minutes on ice, then incubated for 15 minutes in 0.2% Triton X-100 in phosphate-buffered saline (PBS). After three washes in PBS, the cells are incubated in blotting solution (1% BSA and 0.2% Tween 20 in PBS) for 15 minutes. The samples are then treated with one of the following antibodies: anti-Csx (1:100-1:200, from S. Izumo, Harvard Medical School, Boston Mass.), MF-20 (1:50 to 200, from Developmental Studies Hybridoma Bank, University of Iowa, Iowa City Iowa), anti-desmin (1:100-200, from Sigma-Aldrich, Inc., St. Louis Mo.), and, if desired, their isotype controls (for Csx, normal rabbit serum; for MF-20, mouse IgG2b; for desmin, mouse IgG1) at the same concentration, and incubated overnight at 4° C. in a moist chamber. The sample slides are then washed three times using a washing solution (0.5% Tween 20 in PBS) and incubated with secondary antibodies (for Csx, donkey anti-rabbit IgG, for MF-20 and anti-desmin, donkey anti-mouse IgG, all from Jackson ImmunoResearch Laboratories, Inc.) following the instructions provided by the vendors, followed by three washes. The samples are then examined under a fluorescence microscope (e.g., a Nikon TS100 microscope with a matching fluorescence attachments) and visually scored for immunolabeling.

By "cardiac-specific enhancer element" is meant an element, operably linked to a promoter, that directs gene expression in a cardiac cell and does not direct gene expression in all tissues or all cell types. For example, certain cardiac-specific enhancer elements from Csx/Nkx2.5 drive gene expression in cardiac cells as well as in tongue and embryonic stomach. Cardiac-specific enhancers of the present invention may be naturally occurring or non-naturally occurring.

By "heterologous" is meant that the nucleic acid molecule originates from a foreign source or, if from the same source, is modified from its original form. Thus, a "heterologous promoter" is a promoter not normally associated with the duplicated enhancer domain of the present invention. Similarly, a heterologous nucleic acid molecule is modified from its original form or is from a source different from the source from which the promoter to which it is operably linked was derived.

By "substantially pure nucleic acid" is meant nucleic acid that is free of the genes which, in the naturally-occurring genome of the organism from which the nucleic acid of the invention is derived, flank the nucleic acid. The term therefore includes, for example, a recombinant nucleic acid which is incorporated into a vector; into an autonomously replicating plasmid or virus; or into the genomic nucleic acid of a prokaryote or a eukaryote cell; or which exists as a separate molecule (e.g., a cDNA or a genomic or cDNA fragment produced by PCR or restriction endonuclease digestion) independent of other sequences. It also includes a recombinant nucleic acid that is part of a hybrid gene encoding additional polypeptide sequence.

By "transgene" is meant any piece of a nucleic acid molecule (for example, DNA) that is inserted by artifice into a cell either transiently or permanently, and becomes part of the organism if integrated into the genome or maintained extrachromosomally. Such a transgene may include a gene that is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression vector operably linked to a heterologous nucleic acid molecule can be used to produce a population of cells having altered phenotypic characteristics. A cell derived from a transgenic organism is also a transgenic cell so long as the cells contains the transgene.

Other features and advantages of the invention will be apparent from the following description of the preferred embodiments thereof, and from the claims.

BRIEF DESCRIPTION OF DRAWINGS

The application file contains drawings executed in color (FIGS. 2-14). Copies of this patent or patent application with color drawings will be provided by the Office upon request and payment of the necessary fee.

FIG. 4 is a series of micrographs showing the morphology and Csx/Nxk2.5 expression of canine BMSCs following in vitro differentiation.

FIG. 15 is a pair of micrographs comparing β-galactosidase activity in hCsx-lacZ mouse BMSCs which are cultured in the absence (left panel) or presence (right panel) of growth factors which induce cardiomyogenic differentiation.

FIGS. 17-19 show echocardiograms of infarcted canine heart before (left panels) and after (right panels) induced BMSC transplantation.

FIG. 21A is a schematic illustration of an exemplary three barrel, two needle syringe having one larger barrel for injection of one cell type. The two smaller barrels connect to a reservoir adaptor that is connected to one needle. The larger barrel has a separate needle for injection. It is desirable that the needle hole of the needle connected to the larger barrel is increased to maintain the barrel/needle hole ratio of the smaller barrels, thereby maintaining equal injection pressure in all three barrels. While optional, the triangular arrangement of the three barrels allows close proximity of the two needles, while maintaining a parallel injection angle. The three syringe barrels are connected at the top and are controlled by a single plunger depressor for even injection pressure.

FIG. 21B is a schematic illustration of a cross-section of the three barrel, one needle syringe of FIG. 21A.

DETAILED DESCRIPTION OF THE INVENTION

Figure 1:
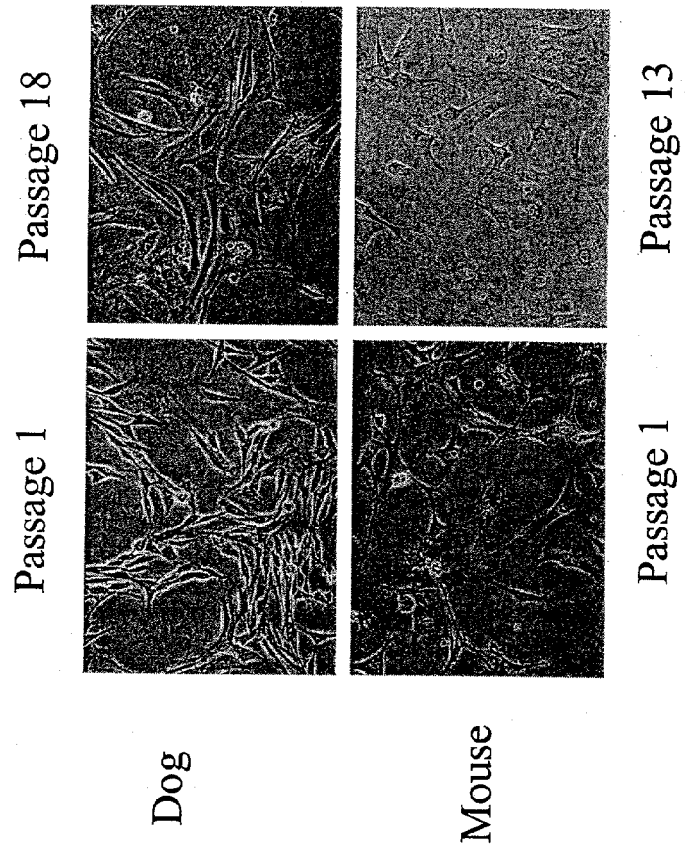
FIG. 1 is a phase contrast micrograph of isolated, cultured bone marrow stem cells from mouse and dog.

We have discovered that transplanting developmentally committed but undifferentiated cells will improve the survival, incorporation, and adaptation of the implant in the target tissue.

In developing vertebrates, the early cardiac field is defined by the expression of the Csx/Nkx2.5 gene. At this developmental stage, however, the Csx/Nkx2.5-expressing cells are still proliferating. We believe that the transplantation of Csx/Nkx2.5-expressing cells that are still proliferating will result in an increased number of incorporated and functional cardiomyocytes in the heart.

We have also discovered a therapeutic cellular transplantation method in which blood vessels and myocardial tissue are collectively regenerated in the area of treated myocardium. This method includes the transplantation of undifferentiated cells committed to become one of three cell types: cardiomyocytes, endothelial cells, or vascular smooth muscle cells.

It is desirable that there be an ample supply of the cells to be transplanted. Accordingly, in one aspect, the cells to be transplanted are derived from stem cells. One suitable stem cell is the BMSC, which can be isolated from adult bone marrow. Once isolated, BMSCs can be treated with growth factors (referred to herein as "priming") to induce the cells toward a cardiomyocyte cell lineage, as is described below. Alternatively, BMSCs can be primed toward an endothelial cell lineage, or a vascular smooth muscle cell lineage. In one embodiment, the BMSCs are monitored for lineage conversion using a cognate cell type-specific indicator system, such as the one described in U.S. Provisional Application Ser. No. 60/283,837, hereby incorporated by reference. To generate the cell type-specific indicator system, transgenic mouse lines are established using a gene construct that includes a cell lineage-specific enhancer/promoter-driven marker. For example, cardiomyocyte progenitor conversion can be monitored using encapsulated BMSCs from hCsx-LacZ transgenic mice. Once adequate marker gene expression is detected in the cell population, the cells are collected and injected into the host myocardium.

In one embodiment, the cardiomyocyte progenitor cells, endothelial progenitor cells, and vascular smooth muscle cells are injected simultaneously into the host myocardium. For a proper distribution of each cell types in desired areas, a multi-channeled syringe that is designed to inject multiple cell types can be used. The length of each of the needles and the distance between them can be adjusted according to the optimal locations of each cell types in the myocardium to be repaired.

Optimization of stem cells and stem cell derivative preparations is critical for successful cell transplantation. To achieve maximum yield in cell transplantation, the implanted cells are desirably at the proper stage of commitment and differentiation. Currently, despite the known commitment and differentiation markers for many animal cells, it is difficult to determine the proper time to harvest cells during in vitro culture without performing time-consuming molecular biological assays for the expression of these markers. We have discovered a biologically active indicator system with which to determine, in real time, the differentiation state of cells in culture. This indicator system is also useful, for example, for determining the amount of gene expression of proteins during cell growth or cell death.

Most tissue-specific gene expression is controlled by enhancer and repressor sequences at the transcriptional level. Generally, to confer tightly-regulated expression, enhancers adopt complex regulatory mechanisms that require the collaboration of multiple transcription factors. The binding sites for these transcription factors may be many kilobases (kb) from the gene promoter and dispersed relative to each other.

When used to drive transgene expression in mice, cardiac enhancers from hCsx/Nkx2.5 and mCsx/Nkk2.5 recapitulate expression patterns of the endogenous mCsx/Nkx2.5 (see, e.g., U.S. Patent Application Publication No. 2002022259, hereby incorporated by reference). Among the mammalian cardiac enhancers known so far, one of these enhancers (the 7.5 kb enhancer) is the earliest enhancer that is active in all four heart chambers. Moreover, this enhancer displays no ectopic expression. Within this 7.5 kb fragment, two regions (referred to herein as homology domain A1 and homology domain A2 were isolated that together, when operably linked to an hsp68 promoter-lacZ cassette, were capable of enhancing gene expression in a cardiac-specific manner. These two regions can also be used in the reporter constructs of the invention.

EXAMPLE 1

Induction of Cardiomyogenic Cells from BMSCs

Figure 3:
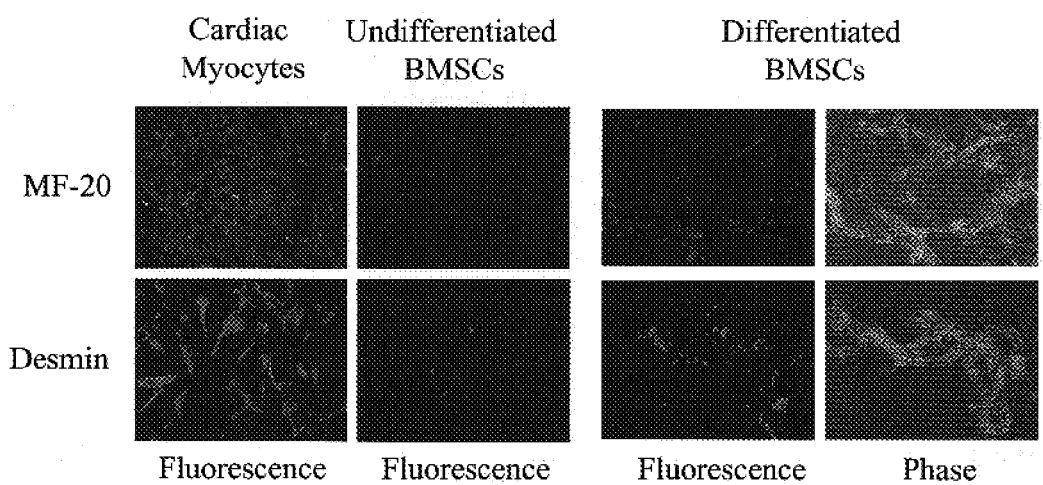
FIG. 3 is a series of micrographs showing the staining and morphology of murine cardiomyocytes, undifferentiated BMSCs, and differentiated BMSCs using the MF-20 antibody, specific for sarcomeric myosin, or an anti-desmin antibody.

Marrow was isolated from adult mouse and dog. The BMSCs were isolated and cultured in medium containing 10% fetal bovine serum, 100 μM L-ascorbic acid-2-$PO_4$, 5-15 ng/ml leukemia inhibitory factor (LIF), and 20 nM dexamethasone (for mouse cultures, mouse LIF was used, while for dog cultures, human LIF was used). This in vitro condition allows the BMSCs to maintain their self-renewing character and to expand by passaging without losing responsiveness to the differentiation agents such as growth factors. Further, stem cells cultured through multiple passages maintain a mesenchymal morphology and karyotype (FIG. 1). After 14 days in culture with growth factors (50 ng/ml BMP2, 100 ng/ml bFGF), approximately 80% of the BMSCs were positively stained with Csx/Nkx2.5, MF-20 (a monoclonal antibody specific for sarcomeric myosin), and desmin antibodies, indicating that the cells had differentiated as cardiomyocytes (FIGS. 3 and 4).

Figure 2:
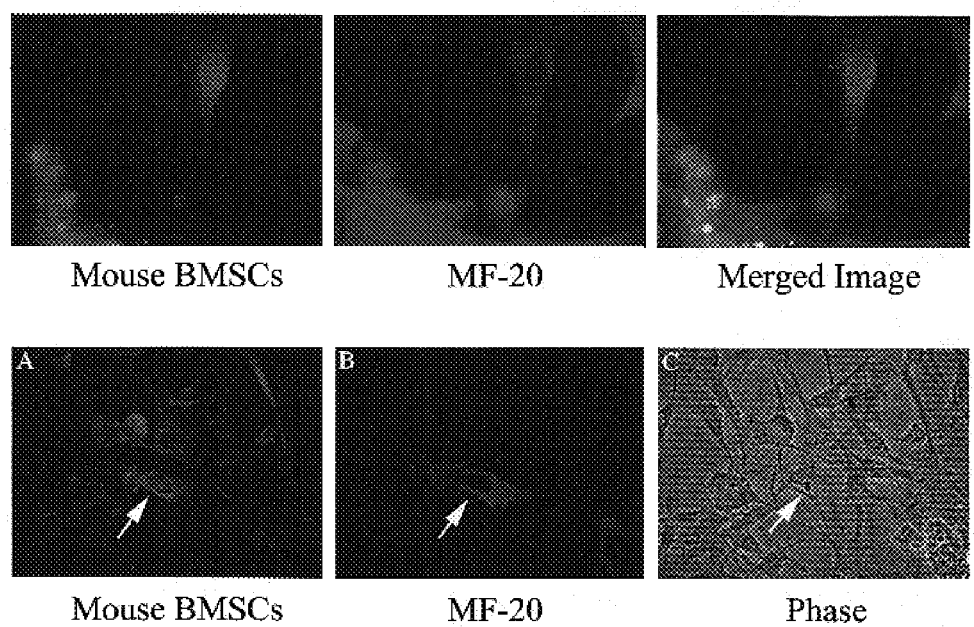
FIG. 2 is a series of micrographs showing murine BMSCs following a 14 day co-culture with chicken cardiomyocytes.

To mimic the environment of the adult myocardium to which transplanted BMSCs are exposed, a co-culture model system was used. In this system, BMSCs, labeled with a fluorescent tag for identification (Vybrant™), and primary chicken embryonic cardiomyocytes were co-cultured, at a ratio of 1:40, on glass slides coated with 5 ng/ml collagen. These mixed cultures were grown alone, in the presence of 25 ng/ml BMP2, or in the presence of 25 ng/ml bFGF. Cells were subsequently stained with anti-Csx/Nkx2.5, MF-20 (a monoclonal antibody specific for sarcomeric myosin), and anti-desmin antibodies. Five days after the initiation, a few (0.1-1%) myosin-positive cells were detected in co-cultures grown in the presence of BMP2 or bFGF, while co-cultures grown in the absence of either growth factor were negative for all three antibodies. However, after two weeks of co-culture in the absence of growth factors, numerous BMSCs were MF-20-positive, suggesting they had converted to a myogenic cell lineage (FIG. 2). Thus, BMSCs can be induced to differentiate along a myogenic lineage using either growth factors such as BMP2 and bFGF, or by co-culture with differentiated cardiomyocytes.

In view of the foregoing results, we can regulate the rate and amount that BMSCs become cardiomyogenic cells in culture by modulating the environment in which the cells are cultured. According to the transplantation method of the invention, it is desirable that at least 10% of the transplanted cells be cardiomyogenic cells (i.e., mitotic cells that express Csx/Nkx2.5 but do not show organized sarcomeric structures or contractions, and preferably do not express detectable amounts of myosin heavy chain RNA or protein). A higher percentage cardiomyogenic cells will result in increased incorporation of implanted cells. Thus, is it desirable that at least 10%, 25%, 50%, 75%, 85%, 90%, or 95% or more of the cells be cardiomyogenic cells. Real-time measurement of commitment can be performed using the cell indicator system described in Example 5, below.

EXAMPLE 2

BMSCs From Humans and Other Mammals

The foregoing example utilizes mouse BMSCs for illustrative purposes. Human BMSCs are also known in the art to be capable of producing cardiac cells (Pittenger et al., Science 284: 143-147, 1999). BMSCs from other mammals (e.g., humanized pig BMSCs) can also be used in the methods of the invention (Levy et al., Transplantation 69: 272-280, 2000).

EXAMPLE 3

Methods of Inducing BMSCs to Become Cardiomyogenic

As is described above, co-culturing BMSCs with cardiomyocytes in the presence of BMP2 and/or bFGF results in the induction of cardiomyogenic cells capable of differentiating as cardiomyocytes in culture. The ratio of BMSCs to inducer cells and the concentration of growth factor(s) can each be adjusted to modulate the rate and amount of cardiomyogenic cell induction. For example, the ratio of BMSCs to inducer cells can range from about 1:1 to about 1:1000 or more. The concentration of BMP2 can range from about 0.5 ng/ml to about 1 μg/ml, while the concentration of bFGF can range from about 1 ng/ml to about 5 μg/ml. It is understood that other BMP/TGFβ and FGF family members can be used instead of BMP2 and/or bFGF.

Other methods known to induce BMSCs to become cardiomyogenic cells can be used in the present invention. Not all methods that induce cardiomyocytes can be used in the invention. For example, 5-azacytidine is used as the inducing agent for cardiomyocytes (Makino et al., J. Clin. Invest., 103: 697-705, 1999) but is not appropriate in the methods of the invention. Since 5-azacytidine randomly demethylates genomic sequences (thereby inducing normally silent genes), treatment of the BMSCs with 5-azacytidine can generate a variety of cell types (e.g., myocytes (MyoD positive), osteoblasts (osteocalcin positive), and adipocytes (PPAR-γ positive)), in addition to cardiomyocytes (cardiac troponin I positive) (Wakitani et al., Muscle Nerve, 18: 1417-1426, 1995; Tomita et al., Circulation, 100 suppl II: 247-256, 1999). BMSCs exposed to 5-azacytidine are known to rapidly upregulate c-abl and interleukin-6 transcripts while downregulating the expression of collagen I, a major matrix protein. (Andrews et. al., Mol. Cell. Biol., 9: 2748-2751, 1989). In the methods of the invention, suitable factors or conditions are those that specifically induce one cell type (e.g., cardiomyocytes).

EXAMPLE 4

Induction of Other Cell Types

It may be desirable to induce cells types such as vascular smooth muscle cells and endothelial cells (or their precursors) for transplantation into the myocardium because theses cells may generate new blood vessels around the transplanted cardiomyogenic cells. The cells can be transplanted alone, but preferably are transplanted with the appropriate cardiomyogenic cells, as described herein.

Differentiation of vascular smooth muscle cells can be determined using the Bves gene enhancer (Reese et al., Dev. Biol. 209: 159-171, 1999). Differentiation of endothelial cells can be determined using Tie-2 or von Willebrand Factor enhancers that have been cloned (Schnurch and Risau, Development 119: 957-968, 1993 and Coffin et. al., Dev. Biol. 148: 51-62, 1991, respectively). Differentiation of embryonic epicardial cells (i.e., precursors of endothelial cells) can be determined using Flk-1 or ICAM-2 enhancers (Shalaby et al., Nature 376:62-66,1995 and Tevosian et al., Cell 101:729-739, 2000, respectively).

Figure 5:
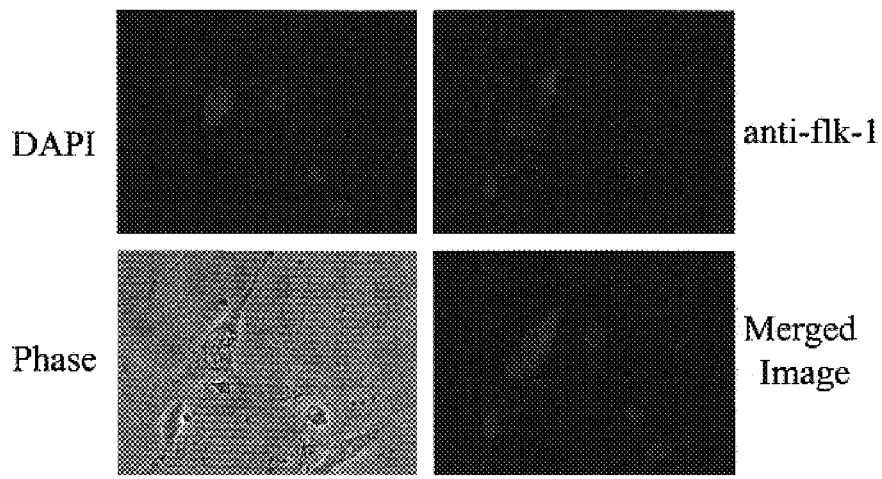
FIG. 5 is a series of micrographs demonstrating in vitro differentiation of murine BMSCs into cells of endothelial lineage.

BMSCs were isolated as describe above and cultured in the presence of biological factors known to generate endothelial cell lineages during embryonic development (2% FBS, 20 ng/ml VEGF, 1 ng/ml bFGF, and 2 ng/ml IGF-I). Flk-1, an endothelial-specific receptor tyrosine kinase, was robustly expressed in approximately 80% of cultured BMSCs, after 14 days in culture, indicating conversion to an endothelial cell lineage (FIG. 5).

EXAMPLE 5

Cell Indicator System

Figure 16A:
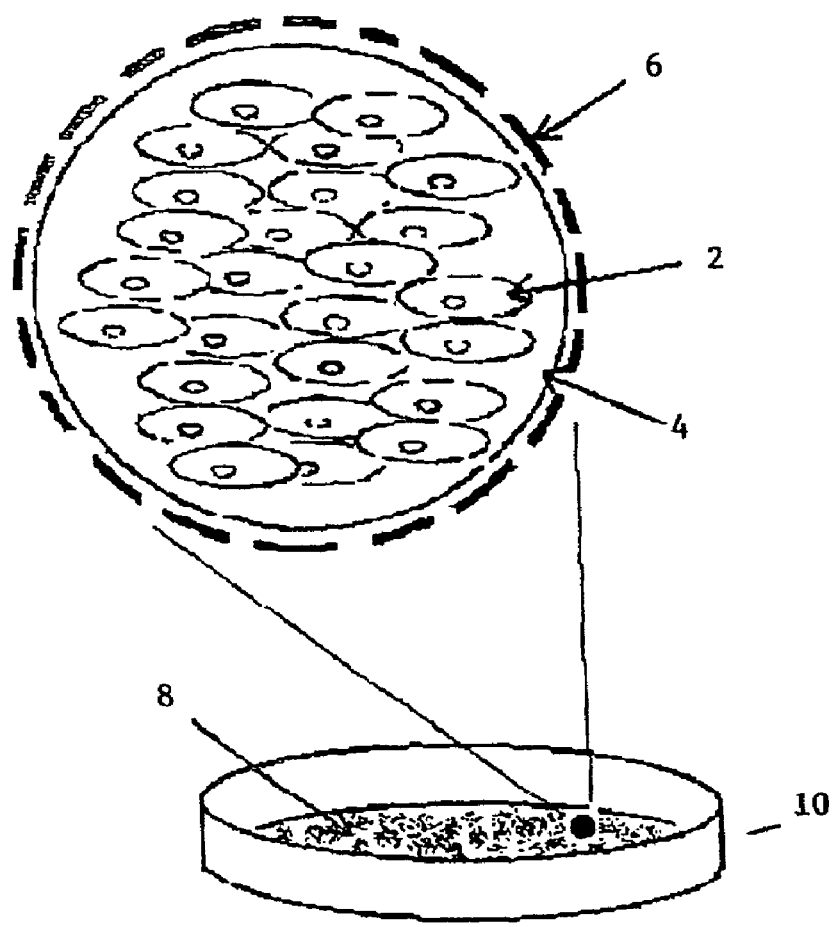
FIG. 16A shows an exemplary encapsulated cell indicator system. In the illustration, the indicator cells 2 are encapsulated in an encapsulating material 4 such as alginate beads. The indicator cells 2 and encapsulating material 4 are contained in a permeable membrane or mesh 6 and co-cultured with cells 8 in a culture vessel 10.
Figure 16:
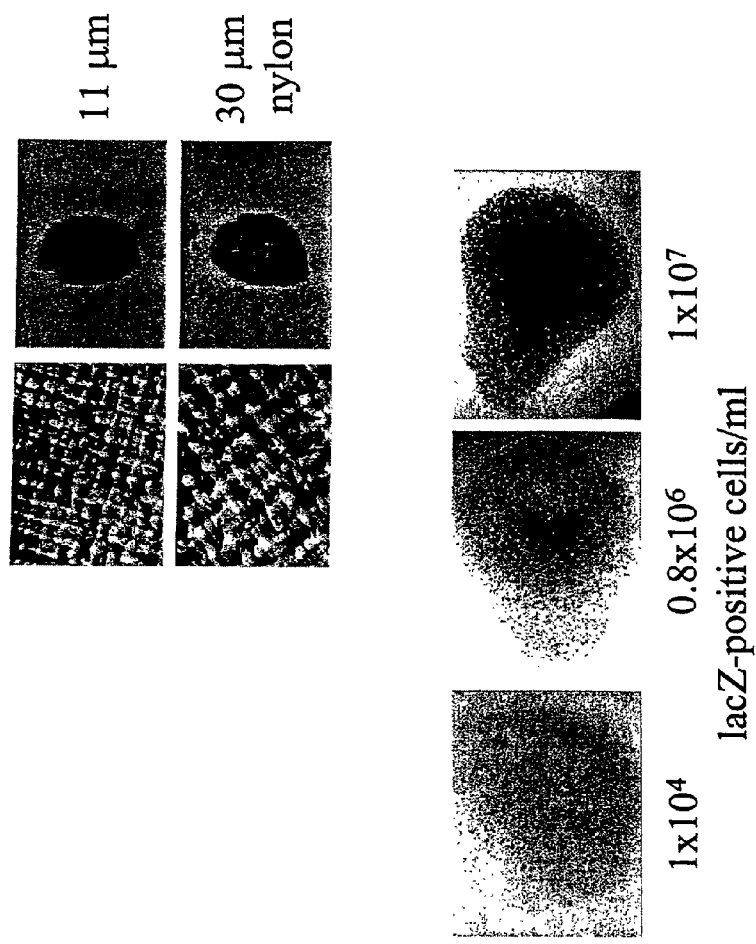
FIG. 16B shows the use of encapsulating indicator cells to monitor myogenic differentiation in culture. Shown are micrographs of 11 μm and 30 μm nylon mesh, suitable for cell encapsulation; and micrographs showing the results of the β-galactosidase reaction performed using hCsx-lacZ mouse BMSC indicator capsules containing varying cell numbers.
Figure 20A:
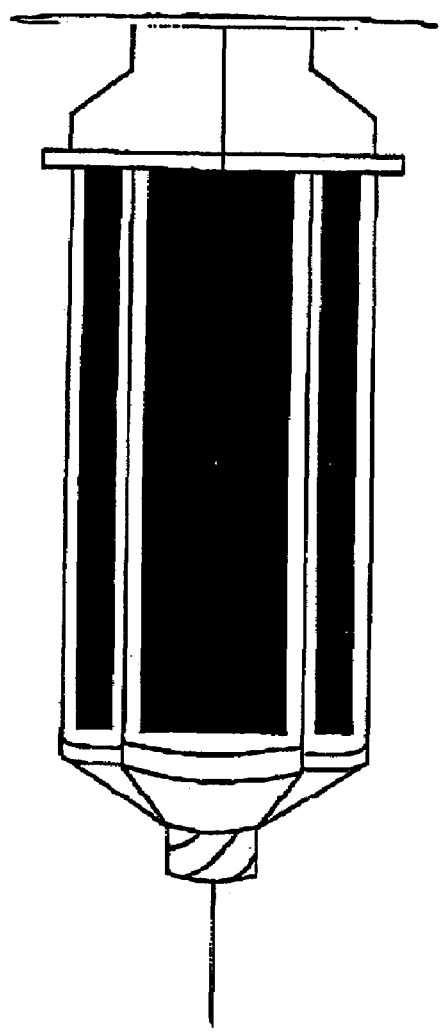
FIG. 20A is a schematic illustration of an exemplary three-barrel, one needle syringe. In this example, each barrel is injected simultaneously and evenly into a reservoir adaptor that is connected to a single needle for a precise injection location. The three syringe barrels are connected at the top and are controlled by a single plunger depressor.
Figure 20B:
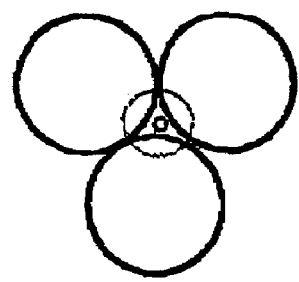
FIG. 20B is a schematic illustration of a cross-section of the three-barrel, one needle syringe of FIG. 20A.
Figure 22A:
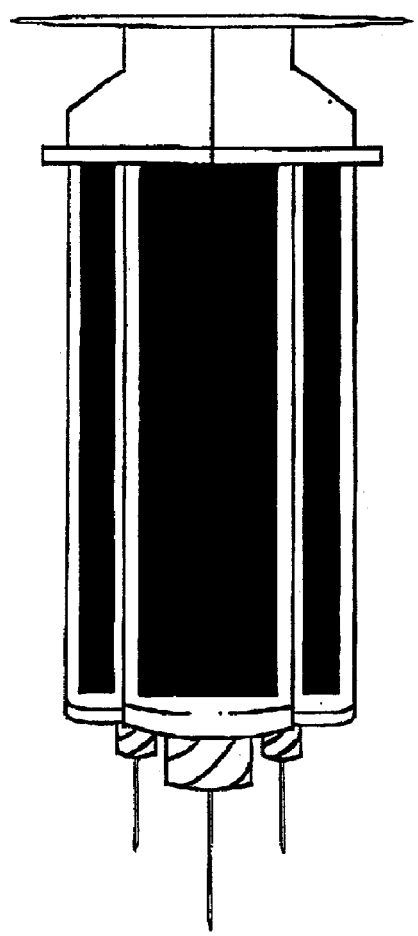
FIG. 22A is a schematic illustration of an exemplary three barrel, three needle syringe design in which the each syringe barrel has its own needle for injection. If desired, the triangular arrangement of the three barrels allows close proximity of the three needles while maintaining a parallel injection angle. The three syringe barrels are connected at the top and are controlled by a single plunger depressor for even injection pressure.
Figure 22B:
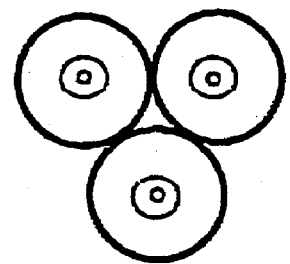
FIG. 22B is a schematic illustration of a cross-section of the three barrel, one needle syringe of FIG. 22A.

As depicted in FIG. 16A, the indicator system includes three components: indicator cells 2, a cell encapsulation system (CES) 4, and a permeable outside membrane or mesh 6 that helps retain the indicator cells in the CES and separates the indicator cells 2 from those to be transplanted 8.

In one example, the indicator system is useful in determining the state of cell commitment and differentiation of stem cells (e.g., BMSCs). As is described herein, it is desirable to prime human BMSCs such that about 5-100% (preferably about 80%) of the cells are cardiomyogenic cells (as determined by Csx/Nkx2.5 expression, the lack of organized sarcomeric structures or contractions, and preferably, the lack of myosin heavy chain RNA or protein). Thus, an extremely rapid assay is desired in order to minimize the time interval between harvesting the cells for the assay and transplantation. A rapid assay, therefore, ensures that the assay results are representative of the Csx/Nkx2.5-expressing cells which are ultimately transplanted. The present invention provides such an assay. BMSCs from transgenic mice containing a Csx enhancer operably linked to a reporter gene are used as indicator cells. Suitable Csx enhancers are described, for example, in U.S. Patent Application Publication No. 2002022259, hereby incorporated by reference. The indicator cells are either encapsulated in a biological material (e.g., alginate, collagen, gelatin, or chitosan) or attached onto a biodegradable polymer (e.g., non-porous microspheres of polylactic acid (PLA), polyglycolic acid (PGA), or polylactide/glycolide copolymer (PLGA)). The encapsulated or microsphere-attached cells are then surrounded by a membrane that permeable to oxygen, nutrients, and other biomolecules. Examples of suitable membranes include porous transparent polyethylene terephthalate (PET) membrane, transparent nylon mesh, transparent porous nylon membrane, and porous transparent polytetrafluoroethylene (PTFE/Teflon).

In addition to retaining the indicator cells in the capsule, the outer membrane provides a physical integrity to the system. During the induction of the human BMSCs into cardiomyogenic cells, the reporter gene operably linked to the Csx enhancer (e.g., a human Csx enhancer) will be expressed in the indicator cells. Nontoxic detection of reporter gene expression indicates the differentiation state of the human cells. Suitable reporter genes include, without limitation, those encoding green fluorescent protein, $\beta$-galactosidase, and luciferase. After determining that the cells have reached the desired state of differentiation, the entire indicator system (including the indicator cells, the encapsulating material, and permeable membrane) is removed. The cells to be implanted are then collected and prepared for transplantation. If desired, the cells can be frozen and stored until transplantation.

In the cell indicator system of the present invention, the indicator cells can be any cell type in which the enhancer element/reporter gene construct is operable as the cells differentiate. In one example, BMSC cells transfected with the reporter construct are used. These cells can be any animal BMSCs or, alternatively, other cell types such as ES cells transfected with enhancer element/reporter gene construct, or BMSCs from an enhancer element/reporter gene transgenic animals.

We demonstrate the principles described above, of an encapsulated cell indicator system, using murine BMSCs derived from hCsx-lacZ transgenic mice. We have found that BMSCs which are not induced to differentiate along a cardiomyogenic lineage stain weakly or not at all following a standard $\beta$-galactosidase assay. (FIG. 15). In contrast, BMSCs cultured according to the methods described above, which induce cardiomyogenic differentiation, produce a strongly positive signal (FIG. 15). Accordingly, the murine hCsx-lacZ BMSCs are excellent candidates for encapsulation as a system that can be used to monitor the progression of myogenic differentiation (FIGS. 16A and 16B). Such an indicator system provides several advantages over traditional techniques for assessing cell differentiation. Specifically, the capsules are easily recovered from the culture media and can be rapidly and reliably assayed. Further, because the capsule can be incorporated and recovered from every culture vessel, monitoring can be done on a plate-by-plate basis. It is not necessary to destroy an entire culture for monitoring purposes, as is required using traditional histological techniques. This is particularly important when using BMSCs from a human patient where bone marrow samples are difficult to obtain and few stem cells are available for culture and transplantation.

Murine hCsx-lacZ BMSCs can be encapsulated in any appropriate material whose properties are described above. Useful capsules can be made, for example, by embedding the cells in alginate and containing the alginate-embedded cells in 11 µm or 30 µm nylon mesh, available, for example, from Millipore Corp. (Bedford, Mass.), which is both durable and permeable to culture media and growth factors, oxygen, and chemical reagents used in the $\beta$-galactosidase assay. Using the methods described herein, capsules are desirably formed in solutions containing at least about $10^6$ hCsx-lacZ BMSCs per milliliter; however the use of at least about $10^7$ cells/ml is more desirable. Of course, as conditions vary, a person of ordinary skill could determine the appropriate concentration of indicator cells in the capsule system.

The specific indicator cells used to create the encapsulated monitoring system on this invention need not be murine cells. The indicator cells can be either heterologous or autologous to the transplant recipient. In cases where BMSCs are relatively plentiful, it is preferable to transfect a subset of the host BMSCs with a reporter construct, such as the one previously described. These autologous BMSCs are then encapsulated and used for monitoring purposes. Alternatively, in cases where BMSCs are in limited supply, non-autologous (homologous or heterologous) indicator BMSCs can be used.

EXAMPLE 6

Methods for Transplantation

The invention pertains to methods for treating disorders characterized by insufficient cardiac function in a subject by autologous or heterologous cardiac cell transplantation. The methods include administering to the subject the stem cell-derived cardiomyocyte progenitors, endothelial cell progenitors, and vascular smooth muscle progenitors of the invention, which are described in detail herein. Transplantation of the cells of the invention into the heart of the subject with a cardiac disorder results in replacement of lost or non-functioning ("hybernating") cardiomyocytes. The cells are introduced into a subject with a cardiac disorder in an amount suitable to replace lost or non-functioning cardiomyocytes such that there is an at least partial reduction or alleviation of at least one adverse effect or symptom of the cardiac disorder. The cells can be administered to a subject by any appropriate route that results in delivery of the cells to a desired location in the subject where at least a portion of the cells remain viable. It is desirable that at least about 5%, desirably at least about 10%, more desirably at least about 20%, yet more desirably at least about 30%, still more desirably at least about 40%, and most desirably at least about 50% or more of the cells remain viable after administration into a subject. The period of viability of the cells after administration to a subject can be as short as a few hours, e.g., twenty-four hours, to a few days, to as long as a few weeks to months. One method that can be used to deliver the cells of the invention to a subject is direct injection of the cells into the ventricular myocardium of the subject (e.g., Soonpaa et al., Science 264:98-101, 1994; Koh et al., Am. J. Physiol. 33:H1727-1733, 1993). The cells can be administered in a physiologically compatible carrier, such as a buffered saline solution. To treat disorders characterized by insufficient cardiac function in a human subject, about $10^4$-$10^9$ cells are introduced into the human, e.g., into the myocardium.

To accomplish these methods of administration, the cells of the invention can be inserted into a delivery device that facilitates introduction by injection or implantation of the cells into the subject. Such delivery devices include tubes, e.g., catheters, for injecting cells and fluids into the body of a recipient subject. In a preferred embodiment, the tubes additionally have a needle or needles through which the cells of the invention can be introduced into the subject at a desired location. It may be desirable to maintain each cell type in a different set of conditions (such as in different media) during the injection. In such a case, a multi-barrel syringe with one, two, or three needles can be used for injection (FIGS. 20A, 20B, 21A, 21B, 22A, and 22B). If a three-barrel/two-needle syringe is used, it is preferable that endothelial cell progenitors and smooth muscle cell progenitors be mixed during the injection.

The cells of the invention can be inserted into such a delivery device in different forms. For example, the cells can be suspended in a solution or embedded in a support matrix when contained in such a delivery device. Preferably, the solution includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, or thimerosal. Solutions of the invention can be prepared by incorporating the cells as described herein in a pharmaceutically acceptable carrier or diluent and, as required, other ingredients.

Support matrices in which the cells of the invention can be incorporated or embedded include matrices which are recipient-compatible and which degrade into products that are not harmful to the recipient. Natural and/or synthetic biodegradable matrices are examples of such matrices. Natural biodegradable matrices include, for example, collagen matrices and alginate beads. Synthetic biodegradable matrices include synthetic polymers such as polyanhydrides, polyorthoesters, and polylactic acid. These matrices provide support and protection for the cells in vivo.

Prior to introduction into a subject, the cells can be modified to inhibit immunological rejection. For example, to inhibit rejection of transplanted cells and to achieve immunological non-responsiveness in a transplant recipient, the method of the invention can include alteration of immunogenic antigens on the surface of the cells prior to introduction into the subject. This step of altering one or more immunogenic antigens on the cells can be performed alone or in combination with administering to the subject an agent that inhibits T cell activity in the subject. Alternatively, inhibition of rejection of the transplanted cells can be accomplished by administering to the subject an agent that inhibits T cell activity in the subject in the absence of prior alteration of an immunogenic antigen on the surface of the transplanted cells. An agent that inhibits T cell activity is defined as an agent which results in removal (e.g., sequestration) or destruction of T cells within a subject or inhibits T cell functions within the subject. T cells may still be present in the subject but are in a non-functional state, such that they are unable to proliferate or elicit or perform effector functions (e.g., cytokine production, cytotoxicity, etc). The agent that inhibits T cell activity may also inhibit the activity or maturation of immature T cells (e.g., thymocytes). A preferred agent for use in inhibiting T cell activity in a recipient subject is an immunosuppressive drug that inhibits or interferes with normal immune function. A preferred immunosuppressive drug is cyclosporin A. Other immunosuppressive drugs that can be used include, for example, FK506 and RS-61443. In one embodiment, the immunosuppressive drug is administered in conjunction with at least one other therapeutic agent. Additional therapeutic agents that can be administered include steroids (e.g., glucocorticoids such as prednisone, methyl prednisolone, and dexamethasone) and chemotherapeutic agents (e.g., azathioprine and cyclosphamide). In another embodiment, an immunosuppressive drug is administered in conjunction with both a steroid and a chemotherapeutic agent. Suitable immunosuppressive drugs are commercially available.

In addition to its use in the treatment of cardiac-related disorders, cell transplantation therapy is applicable to a wide variety of diseases and disorders (e.g., Parkinson's disease, diabetes, spinal cord injury, multiple sclerosis). As with transplantation into the myocardium, the transplantation of mitotic cells that are competent and primed to adopt the desired cell fate will likely aid in the integration of the transplanted cells, resulting in more of the desired cells incorporating and surviving in the host tissue. Enhancers useful for the detection of the differentiation, commitment, or competence of a cell lineage are depicted in Table 1, below.

TABLE 1

| Cell Type | Marker | Reference |
|---|---|---|
| Vascular smooth muscle cell | Bves | Reese et al., Dev. Biol. 209: 159-171, 1999. |
| Endothelial cell | Tie-2 | Schnurch and Risau, Development 119: 957-968, 1993. |
|  | von Willebrand | Coffin et al., Dev Biol. 148: 51-62, 1991. |
| Epicardial cell | Flk-1 | Shalaby et al., Nature 376:62-66, 1995. |
|  | ICAM-2 | Tevosian et al., Cell 101:729-39, 2000. |
| Adipocyte | PPAR-g2 | Zhu et al., PNAS 92:7921-7925, 1995. |
| Osteoclast | TRAP | Reddy, J. Bone Miner. Res. 10: 601-606, 1995. |
| Osteoblast | Osteocalcin | Kesterson, Mol Endocrinol. 7:462-467, 1993. |
| Macrophage | CD11b | Dziennis et al., Blood. 85:319-329, 1995. |
| Neuronal progenitor | Nestin | Yamaguchi et al., Neuroreport 11: 1991-1996, 2000. |
| Neuron | Neurofilament | Leconte et al., J Mol Neurosci 5: 273-295, 1994. |
| Astrocyte | GFAP | Nolte et al., Glia. 33:72-86, 2001. |
| Skeletal muscle cell | MyoD | Goldhammer et al., Science 256: 538-42, 1992. |
| Smooth muscle cell | SMHC | Zilberman et al., Circ Res 1998 82: 566-575, 1998. |
| Pancreatic precursor cell | Pdx-1 | Marshak et al., Mol. Cell Biol. 20: 7583-7590, 2000. |
| Pancreatic β-cell | Glucokinase | Jetton, et al., JBC. 269: 3641-3654, 1993. |
| Hepatocyte | α-fetoprotein | Ghebranious, Dev 42:1-6, 1995. |

Each of the foregoing references is hereby incorporated by reference.

EXAMPLE 7

Canine Model of Myocardial Infarction

BMSCs, which were directed toward a cardiogenic cell lineage in vitro, were transplanted into infarcted dog myocardial tissue. The dog myocardial infarction was created by permanent occlusion of the left coronary artery. The infarction was allowed to stabilize for at least two months prior to BMSC transplantation. In order to prevent immunorejection of the transplants, marrow was collected and BMSCs prepared from the individual transplant recipient dogs as follows. About four weeks after the ligation, after the myocardial infarction had been confirmed using echocardiogram, iliac bone was punctured to aspirate bone marrow. Bone marrow was immediately mixed with heparin, frozen and transported in dry ice to the tissue culture facility, where the bone marrow was thawed at 37° C., perturbated, washed once with regular DMEM, and plated in tissue culture flasks containing culture medium (10% fetal bovine serum, 100 μM L-ascorbic acid-2-PO$_4$, 5-15 ng/ml LIF, and 20 nM dexamethasone). At the time of harvest, BMSCs were labeled with DiI, a red fluorescent marker, to track the survival and progression of the cells following transplantation. The labeled BMSCs were then cultured in the presence of 100 ng/ml bFGF for 4-7 days. Cells (1.5-250 million) were harvested and injected into the infarcted region of the heart.

Figure 6:
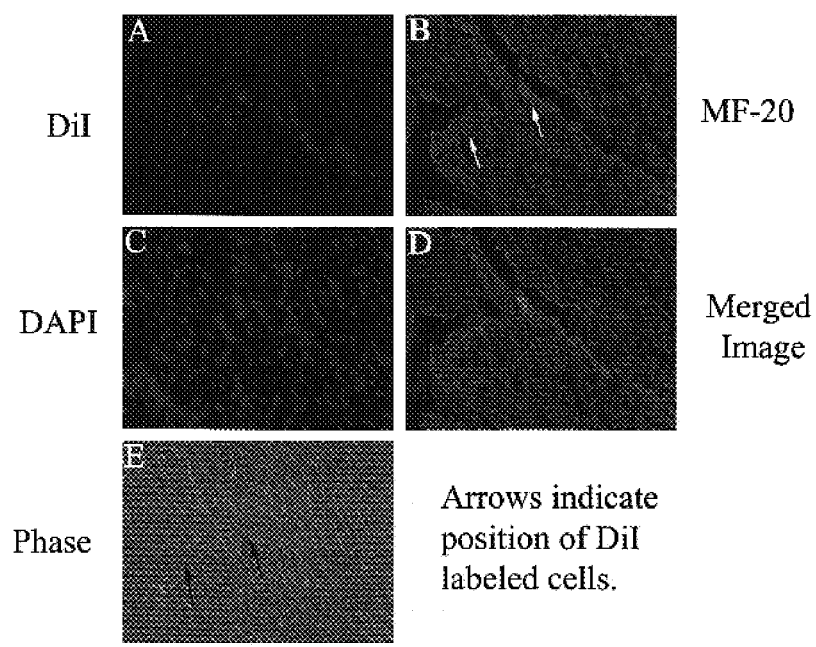
FIG. 6 is a series of micrographs showing the localization of implanted BMSCs in infarcted dog myocardium 15 days after implantation.
Figure 7:
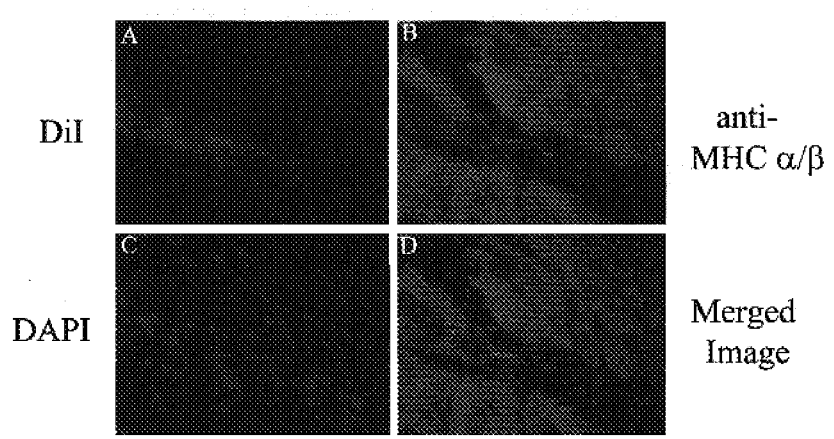
FIG. 7A is a series of micrographs showing the co-localization of implanted BMSCs, by DiI fluorescence, and cardiomyocytes, by anti-MHC α/β fluorescence, in the region in which the cells were injected.
FIG. 7B is a micrograph showing increased survival of BMSCs implanted with a caspase inhibitor, relative to untreated BMSCs.
Figure 8:
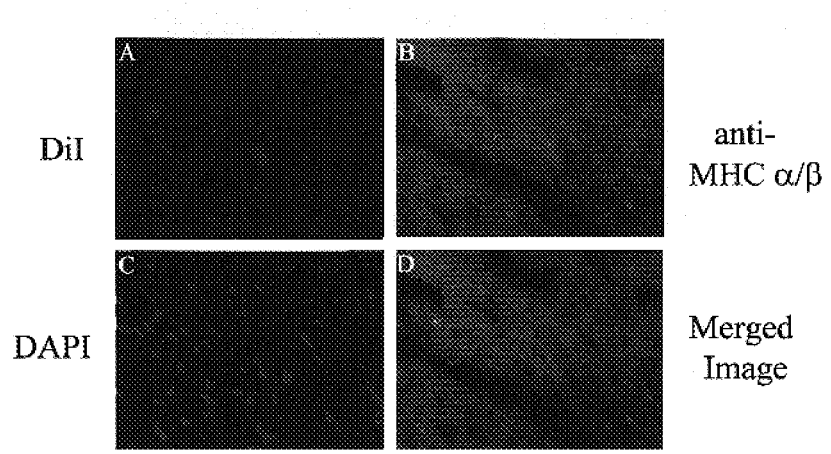
FIG. 8 is a series of micrographs showing the co-localization of implanted BMSCs, by DiI fluorescence, and cardiomyocytes, by anti-MHC α/β fluorescence in a region away from the site of injection.
Figure 9:
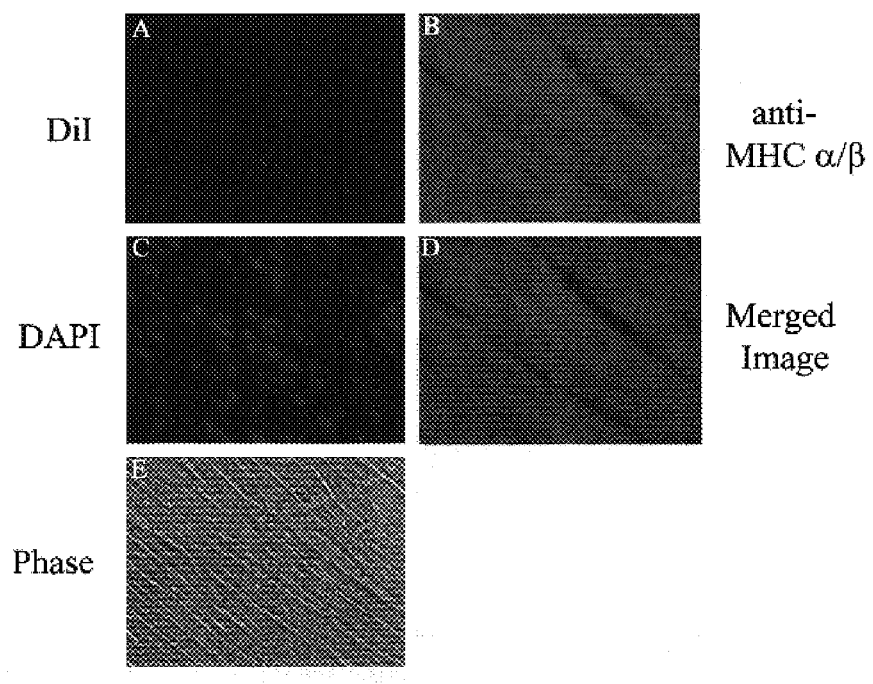
FIG. 9 is a series of micrographs showing the co-localization of implanted BMSCs, by DiI fluorescence, and cardiomyocytes, by anti-MHC α/β fluorescence, in a region away from the site of injection.

BMSC survival following transplantation was assessed by post-mortem visualization of DiI fluorescence. Large clusters of DiI-positive cells were observed in the myocardium 15 days after transplantation, suggesting long-term viability of the BMSCs (FIG. 6). Specifically, the DiI-labeled stem cells were observed within regions of the myocardium containing MF-20-positive cardiomyocytes and in the infarcted regions which were devoid of MF-20-positive cardiomyocytes (FIG. 6). Further, the border region of the infarcted area contained DiI positive stem cells which also express the cardiac muscle-specific marker MHC α/β (FIGS. 7-9). Together, these data demonstrate that transplanted BMSCs, which have been conditioned in vitro according to the described methods, survive and incorporate into the host myocardium and express markers characteristic of cardiac differentiation.

EXAMPLE 8

BMSC Implantation Reduces Infarction Size

The canine myocardial infarction model described in Example 7 was used for in vivo assessment, by echocardiogram (ECG), of the restorative effects of BMSC transplantation. ECGs were performed 3.5, 4.5, and 5 weeks after BMSC transplantation (FIGS. 19, 17, and 18, respectively) and compared to pre-implantation ECGs. In each animal, contraction of the infarct area became more synchronized with neighboring area of the myocardium. Thus, the ECG results confirm the histological findings of Example 7 and demonstrate that transplantation of stimulated, cultured BMSCs results in a partial restoration of cardiac tissue following infarction.

EXAMPLE 9

Murine Model of Myocardial Infarction

Figure 10:
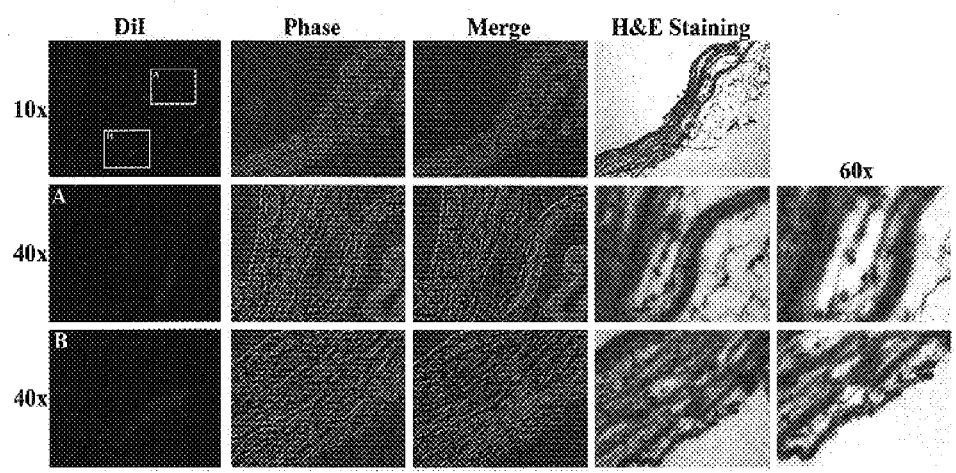
FIG. 10 is a series of micrographs showing the histopathology of the murine myocardial infarction 36 days after BMSC transplantation.
Figure 11:
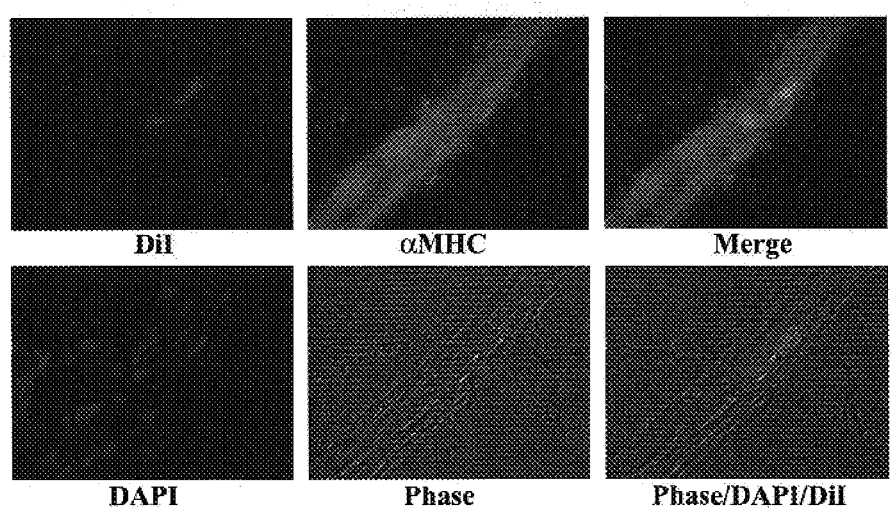
FIGS. 11-14 are micrographs showing the integration of BMSCs into murine myocardial tissue, 36 days after transplantation.
Figure 12:
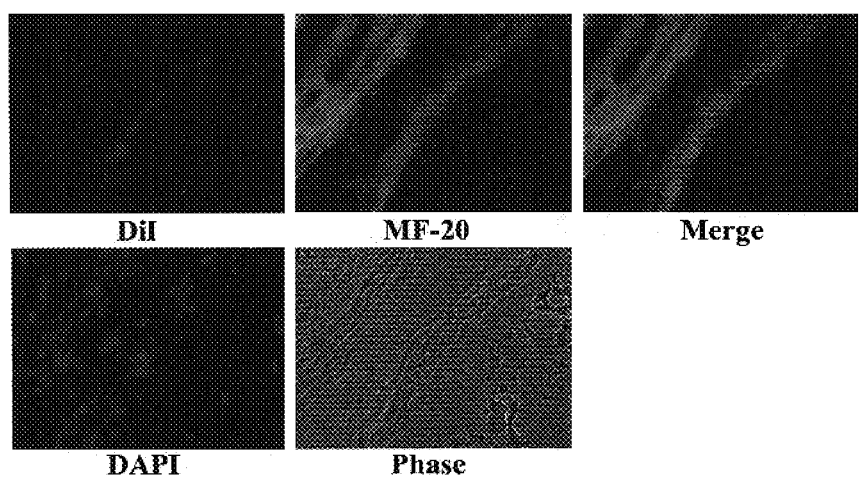
Figure 13:
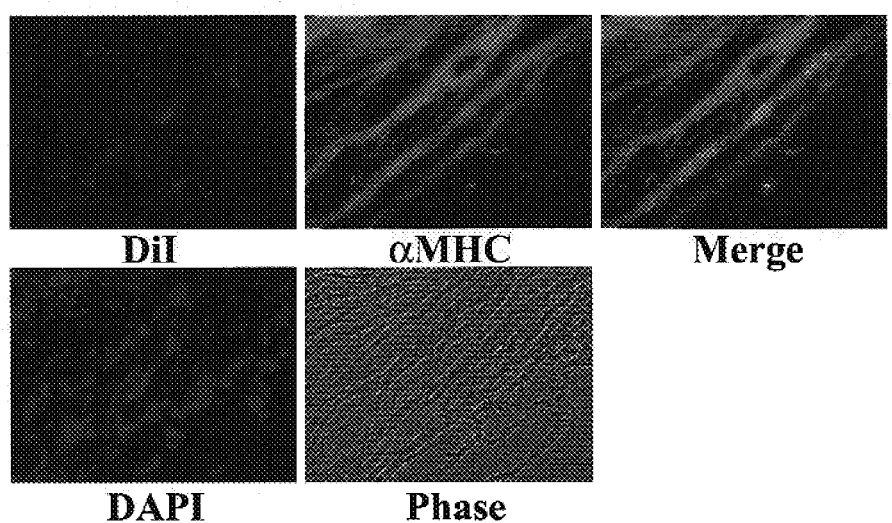
Figure 14:
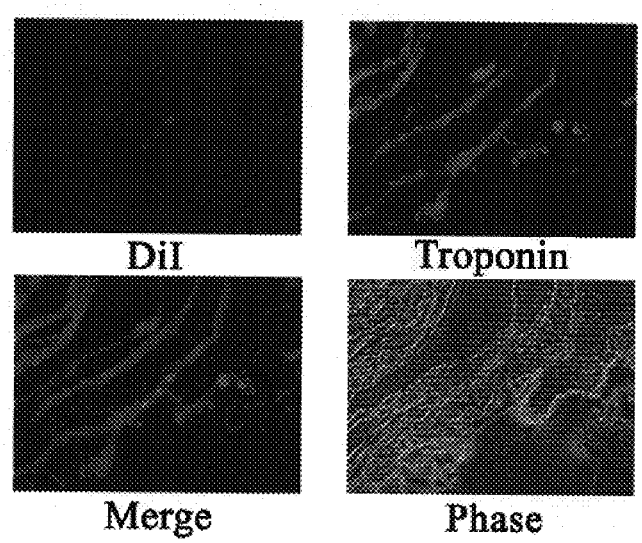

The long-term viability of implanted BMSCs was also investigated using a murine cardiac infarction model system. In order to prevent immunorejection, BMSCs were isolated from marrow collected from mice isogenic to those used for transplantation. As described above, the BMSCs were cultured in the presence of 100 ng/ml bFGF for 4-7 days, then fluorescently labeled with DiI and harvested. Infarctions were created by left coronary artery banding. The treated BMSCs were then injected into the infarction area as follows. BMSCs (100,000 to 500,000 in 10 μl PBS or HBSS) were injected in the anteroseptal LV myocardium in an oblique way, using a 50 microliter Hamilton syringe with a matching 29G or 30G Hamilton needle. During the surgery, the mouse was kept on a custom made heated bed maintained at 37° C. using a feedback temperature controller, and respiration was assisted using a mouse respirator (set volume 200 microliters, 110/min rate). Thirty-six days after transplantation, the infarcted area was analyzed for the presence of DiI-labeled cells and cardiomyocyte viability. As observed in the canine model, labeled BMSCs were incorporated within the murine myocardial infarct. Further, DiI-labeled cells present in the myocardium exhibited morphologies characteristic of cardiomyocytes. Hematoxylin and eosin staining of this region shows striations, corkscrew nuclei, and elongated fibers that are characteristic of cardiac muscle (FIG. 10) inside of the infarct. We also observed DiI-positive cells adjacent to the infracted area of the myocardium. Visualization of cardiomyocytes using α-MHC, MF-20, and cardiac troponin antibody staining demonstrated that the DiI-labeled cells (transplanted BMSCs) were located completely within the cardiac myofibrils (FIGS. 11, 12, and 14). Transplanted BMSCs were also incorporated in the neighboring regions of the myocardium (FIG. 13). Thus, the transplanted stimulated BMSCs fully integrated into both the normal and infarcted cardiac tissue and continued differentiating into cardiomyocytes; a process begun prior to transplantation, during the in vitro stimulation.

EXAMPLE 10

Methods of Inducing Stem Cells to Become Endothelial Progenitor Cells

To generate primed endothelial progenitor cells, isolated stem cells (e.g., human BMSCs) are primed using VEGF (10 ng/ml), bFGF (1 ng/ml), and IGF-I (2 ng/ml) for a period of 4-7 days (Shi et al., Blood 92:362-367, 1998). As a conversion indicator in the cell indicator system, stem cells containing a Tie enhancer operably linked to a reporter gene can be used (Schlaeger et al., Proc. Natl. Acad. Sci. USA 94:3058-3063, 1997).

EXAMPLE 11

Methods of Inducing Stem Cells to Become Vascular Smooth Muscle Progenitor Cells To generate primed vascular smooth muscle progenitor cells, isolated stem cells (e.g., human BMSCs) can be primed using PDGF (1-10 ng/ml) and TGF-β (1-10 ng-ml) for a period of 4-7 days (Hirschi et al., J. Cell Biol. 141:805-814, 2000). As a conversion indicator in the cell indicator system, stem cells containing a Bves enhancer operably linked to a reporter gene can be used (Reese et al, Dev. Biol. 209:159-171,1999).

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. An in vitro encapsulated cell indicator system comprising a culture vessel comprising:
    (a) a first population of bone marrow stem cells (BMSCs) comprising an enhancer element selected from csx, bves, tie-2, von Willebrand, flk-1, ICAM-2, PPAR-γ2, TRAP, osteocalcin, CD11b, nestin, neurofilament, GFAP, myoD, SMHC, pdx-1, glucokinase, and α-fetoprotein enhancer elements, operably linked to a reporter gene;
    (b) encapsulating material;
    (c) a permeable membrane;
    wherein said cells are encapsulated in said encapsulating material, and said encapsulating material and said cells are contained within said permeable membrane; and
    (d) a second population of BMSCs that are separated from said first population by said permeable membrane.

2. The encapsulated cell indicator system of claim 1, wherein said first population of cells comprise human cells.

3. The encapsulated cell indicator system of claim 1, wherein said first population of cells comprise mouse cells or pig cells.

4. The encapsulated cell indicator system of claim 1, wherein said reporter gene encodes β-galactosidase, green fluorescent protein, or luciferase.

5. The encapsulated cell indicator system of claim 1, wherein said encapsulating material comprises alginate, collagen, gelatin, chitosan, polylactic acid, polyglycolic acid, or polylactide/glycolide copolymer.

6. The encapsulated cell indicator system of claim 1, wherein said permeable membrane comprises polyethylene terephthalate membrane, nylon mesh, porous nylon membrane, or porous polytetrafluoroethylene (PTFE/Teflon).

7. The encapsulated cell indicator system of claim 1, wherein said enhancer element is a csx enhancer element.

8. The encapsulated cell indicator system of claim 1, wherein said enhancer element is a tie-2 enhancer element.

9. The encapsulated cell indicator system of claim 1, wherein said enhancer element is a flk-1 enhancer element.

10. The encapsulated cell indicator system of claim 1, wherein said enhancer element is an SMHC enhancer element.

11. An in vitro encapsulated cell indicator system comprising a culture vessel comprising:
    (a) a first population of embryonic stem cells (ES cells) comprising an enhancer element selected from csx, bves, tie-2, von Willebrand, flk-1, ICAM-2, PPAR-γ2, TRAP, osteocalcin, CD11b, nestin, neurofilament, GFAP, myoD, SMHC, pdx-1, glucokinase, and α-fetoprotein enhancer elements, operably linked to a reporter gene;
    (b) encapsulating material;
    (c) a permeable membrane;
    wherein said cells are encapsulated in said encapsulating material, and said encapsulating material and said cells are contained within said permeable membrane; and
    (d) a second population of ES cells that are separated from said first population by said permeable membrane.

12. The encapsulated cell indicator system of claim 11, wherein said first population of cells comprise human cells.

13. The encapsulated cell indicator system of claim 11, wherein said reporter gene encodes β-galactosidase, green fluorescent protein, or luciferase.

14. The encapsulated cell indicator system of claim 11, wherein said encapsulating material comprises alginate, collagen, gelatin, chitosan, polylactic acid, polyglycolic acid, or polylactide/glycolide copolymer.

15. The encapsulated cell indicator system of claim 11, wherein said permeable membrane comprises polyethylene terephthalate membrane, nylon mesh, porous nylon membrane, or porous polytetrafluoroethylene (PTFE/Teflon).

16. The encapsulated cell indicator system of claim 11, wherein said enhancer element is a csx enhancer element.

17. The encapsulated cell indicator system of claim 11, wherein said enhancer element is a tie-2 enhancer element.

18. The encapsulated cell indicator system of claim 11, wherein said enhancer element is a flk-1 enhancer element.

19. The encapsulated cell indicator system of claim 11, wherein said enhancer element is an SMHC enhancer element.

* * * * *

UNITED STATES PATENT AND TRADEMARK OFFICE
CERTIFICATE OF CORRECTION

PATENT NO. : 7,297,538 B2 Page 1 of 1
APPLICATION NO. : 10/121295
DATED : November 20, 2007
INVENTOR(S) : Lee et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 578 days Delete the phrase "by 578 days" and insert -- by 629 days --

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,297,538 B2
APPLICATION NO. : 10/121295
DATED : November 20, 2007
INVENTOR(S) : Lee et al.

It is certified that error appears in the above-identified patent and that said Letters Patent is hereby corrected as shown below:

On the Cover Page, item (56) Under References Cited, line 7, under OTHER PUBLICATIONS, in Shi et al., replace "postive" with --positive--.

On the Cover Page, item (56) Under References Cited, line 8, under OTHER PUBLICATIONS, in Shi et al., replace "reniin" with --rein--.

On the Title Page under item (57), bottom of Abstract "23 Drawing" should read --24 Drawing--.

In the Drawing Sheets, between Sheet 7 of 23 and Sheet 8 of 23, insert Figure 7B -- Figure 7B                                                                                           --.

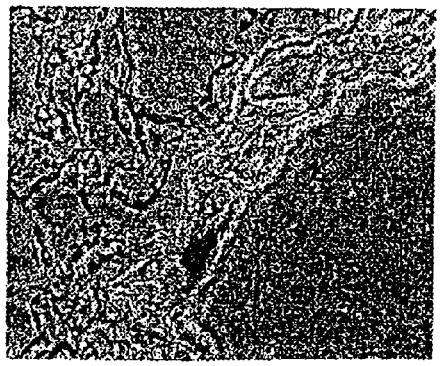
without zVADfmk

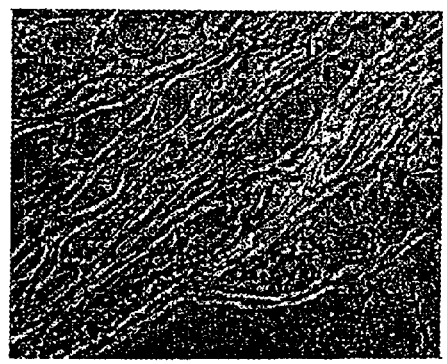
with zVADfmk

UNITED STATES PATENT AND TRADEMARK OFFICE
CERTIFICATE OF CORRECTION

PATENT NO. : 7,297,538 B2
APPLICATION NO. : 10/121295
DATED : November 20, 2007
INVENTOR(S) : Lee et al.

It is certified that error appears in the above-identified patent and that said Letters Patent is hereby corrected as shown below:

Column 9, Line 43, replace "karyotye" with --karyotype--.

Column 13, Line 31, replace "hybernating" with --hibernating--.

Column 15, Line 1, replace "cyclosphosphamide" with --cyclophosphamide--.

Signed and Sealed this

Sixteenth Day of December, 2008

JON W. DUDAS
*Director of the United States Patent and Trademark Office*